(12) United States Patent
Rosendahl et al.

(10) Patent No.: US 8,987,482 B2
(45) Date of Patent: Mar. 24, 2015

(54) PROCESS FOR PRODUCING A SUPPORTED SILVER CATALYST

(71) Applicant: BASF SE, Ludwigshafen (DE)

(72) Inventors: Tobias Rosendahl, Mannheim (DE); Torsten Mäurer, Lambsheim (DE); Cornelia Katharina Dobner, Ludwigshafen (DE); Andreas Lehr, Wachenheim (DE); Johanna Wanka, Darmstadt (DE)

(73) Assignee: BASF SE (DE)

( * ) Notice: Subject to any disclaimer, the term of this patent is extended or adjusted under 35 U.S.C. 154(b) by 147 days.

(21) Appl. No.: 13/661,575

(22) Filed: Oct. 26, 2012

(65) Prior Publication Data

US 2013/0109871 A1  May 2, 2013

Related U.S. Application Data

(60) Provisional application No. 61/552,478, filed on Oct. 28, 2011.

(51) Int. Cl.

| | |
|---|---|
| *B01J 23/50* | (2006.01) |
| *B01J 27/02* | (2006.01) |
| *B01J 21/04* | (2006.01) |
| *B01J 31/22* | (2006.01) |
| *C07F 1/10* | (2006.01) |
| *C07D 301/04* | (2006.01) |
| *C07F 1/00* | (2006.01) |
| *B01J 23/68* | (2006.01) |
| *B01J 35/10* | (2006.01) |
| *B01J 37/02* | (2006.01) |

(52) U.S. Cl.
CPC .............. *C07F 1/005* (2013.01); *B01J 23/688* (2013.01); *B01J 35/1009* (2013.01); *B01J 35/1066* (2013.01); *B01J 35/1076* (2013.01); *B01J 37/0201* (2013.01); *B01J 27/02* (2013.01); *B01J 21/04* (2013.01); *B01J 35/108* (2013.01); *B01J 23/50* (2013.01)
USPC ............................ 549/534; 502/167; 556/116

(58) Field of Classification Search
None
See application file for complete search history.

(56) References Cited

U.S. PATENT DOCUMENTS

| | | |
|---|---|---|
| 3,461,140 A | 8/1969 | Titzenthaler |
| 3,962,136 A | 6/1976 | Nielsen et al. |
| 4,007,135 A | 2/1977 | Hayden et al. |
| 4,324,699 A | 4/1982 | Mross et al. |
| 4,690,913 A | 9/1987 | Nojiri et al. |
| 4,731,350 A | 3/1988 | Boxhoorn et al. |
| 2002/0010094 A1 | 1/2002 | Lockemeyer |
| 2004/0198992 A1 | 10/2004 | Matusz et al. |
| 2004/0198993 A1 | 10/2004 | Matusz et al. |

FOREIGN PATENT DOCUMENTS

| | | |
|---|---|---|
| CN | 101850243 A | 10/2010 |
| CN | 102133544 A | 7/2011 |
| DE | 2454972 A1 | 6/1975 |
| DE | 2300512 C2 | 1/1986 |
| DE | 2521906 C2 | 10/1989 |
| EP | 0014457 B1 | 11/1982 |
| EP | 0085237 B1 | 7/1986 |
| EP | 0082609 B1 | 1/1987 |
| EP | 0172565 B1 | 3/1991 |
| EP | 0266015 B1 | 12/1991 |
| EP | 0339748 B1 | 7/1992 |
| EP | 0357293 B1 | 2/1996 |
| EP | 1613428 B1 | 10/2007 |
| EP | 1115486 B1 | 4/2008 |
| EP | 0716884 B2 | 9/2009 |
| WO | WO-2004/094055 A3 | 1/2005 |
| WO | WO-2007085206 A1 | 8/2007 |
| WO | WO-2009/029419 A1 | 3/2009 |

OTHER PUBLICATIONS

International Search Report for PCT/IB2012/055912, mailing date Mar. 28, 2013.

*Primary Examiner* — Sun Jae Yoo
(74) *Attorney, Agent, or Firm* — Drinker Biddle & Reath LLP

(57) ABSTRACT

Process for producing a supported silver catalyst, which comprises (a) reacting oxalic acid with an alkali metal base in a solvent, preferably water, to the second equivalence point of oxalic acid to give alkali metal oxalate; (b) reacting the alkali metal oxalate obtained according to (a) with silver salt in a solvent, preferably water, to give silver oxalate; (c) forming a complexation of the silver oxalate obtained according to (b) with a diamine compound in a solvent, preferably water, to give a diamine-silver oxalate complex.

16 Claims, 2 Drawing Sheets

PROCESS FOR PRODUCING A SUPPORTED SILVER CATALYST

CROSS-REFERENCE TO RELATED APPLICATIONS

This application claims benefit under 35 U.S.C. §119(e) of U.S. Provisional Patent App. Ser. No. 61/552,478, filed Oct. 28, 2011, which is incorporated herein by reference in its entirety.

The present invention relates to a process for producing a supported silver catalyst, in which process oxalic acid is reacted with an alkali metal base in a solvent to the second equivalence point of oxalic acid to give alkali metal oxalate, the alkali metal oxalate obtained in this way is reacted in a solvent with a silver salt to give silver oxalate and the silver oxalate obtained in this way is complexed with a diamine compound in a solvent to give a diamine-silver oxalate complex. The process of the invention preferably further comprises impregnation of a porous support material with a solution comprising this diamine-silver oxalate complex and preferably calcination of the impregnated porous support material. The present invention likewise relates to the supported silver catalyst which is obtained or obtainable by this process, the precursor thereof and the use thereof for, in particular, preparing ethylene oxide by direct oxidation of ethene by means of oxygen.

In conventional processes for producing supported silver catalysts, in particular supported silver catalysts for preparing ethylene oxide by direct oxidation of ethene in the gas phase, a suitable support, in particular a porous support based on aluminum oxide, is treated with an impregnation solution via which the silver and optionally additional promoters are applied to the support. Silver oxalate is usually prepared as intermediate for producing the impregnation solution, and this is then reacted with a diamine, for example ethylenediamine, to form an ethylenediaminesilver oxalate complex.

As regards the preparation of the silver oxalate, EP 0 716 884 A2, for example, discloses, in the examples, the addition of an aqueous sodium hydroxide solution to an aqueous silver nitrate solution. The precipitate obtained is washed and a predetermined amount of high-purity oxalic acid is then added thereto, with the pH being monitored. It is stated that the pH of the solution should not drop below a value of 7.8. The silver oxalate formed is then concentrated by means of a further filtration. An ethylenediamine solution is then added to this concentrated suspension. Thus, this process involves carrying out concentration by means of filtration twice, which makes the process complicated, especially for implementation on an industrial scale.

A largely identical process is described in EP 1 115 486 A1 and EP 1 613 428 A1, with these documents disclosing that the corresponding pH should be above 7.8. Like EP 0 716 884 A2, neither EP 1 115 486 A1 nor EP 1 613 428 A1 state whether a pH should be set precisely and if so what pH; only certain limits are disclosed. In this process, too, two concentration steps are required.

U.S. Pat. No. 4,731,350 states in quite general terms that silver oxalate can be prepared from a solution of potassium oxalate and silver nitrate. Details of the preparation of potassium oxalate are not disclosed.

WO 2004/094055 A2 and WO 2009/029419 A1 describe a process for producing an impregnation solution, in which silver oxide and oxalic acid are mixed in a first step to give silver oxalate. After isolation and washing, the precipitate is mixed with an aqueous ethylenediamine solution.

As regards the preparation of alkali metal oxalate as starting material for the production of supported silver catalysts, it would in principle be conceivable to add, for example, 2 equivalents of a strong alkali metal base such as potassium hydroxide to one equivalent of oxalic acid, with the experimentally determined purity and thus the starting material quality of the oxalic acid being able to serve as basis for the calculation. However, it has been found that even within a single production batch of oxalic acid such as oxalic acid dihydrate, small quality fluctuations occur. Although these fluctuations may be within the specifications of the manufacturer, they have considerable effects on the quality of the alkali metal oxalate to be prepared and on the process for the preparation thereof.

One of the objects of the present invention was to provide a simplified process which is advantageous on an industrial scale for producing a supported silver catalyst. A further object was to provide improved catalysts, in particular for the preparation of ethylene oxide from ethene and oxygen.

It has surprisingly been found that preparation of alkali metal oxalate by titration of oxalic acid with alkali metal base to the second equivalence point of oxalic acid leads to an improved process and to catalysts having improved catalyst selectivity.

The present invention therefore provides a process for producing a supported silver catalyst, which comprises
(a) reacting oxalic acid with an alkali metal base in a solvent, preferably water, to the second equivalence point of oxalic acid to give alkali metal oxalate;
(b) reacting the alkali metal oxalate obtained according to (a) with a silver salt in a solvent, preferably water, to give silver oxalate;
(c) forming a complex of the silver oxalate obtained as per (b) with a diamine compound in a solvent, preferably water, to give a diamine-silver oxalate complex.

The process of the invention makes it possible to prepare alkali metal oxalate in constant and reproducible quality essentially independently of the purity of the oxalic acid. Fluctuations in the quality of the oxalic acid are compensated in a simple way by the process. In particular, cases in which, for example, a particular purity of the oxalic acid has been determined on the basis of a sample of an oxalic acid batch, this purity is used for determining the equimolar amount of alkali metal base, but a different part of the same batch has a higher or lower purity, are ruled out. In these cases using the conventional method of calculation, actual higher purities could have occurred and led to an excess of oxalic acid after addition of the calculated amount of alkali metal base, which would in turn have led to the precipitation of silver oxalate (see above, step (b)) being carried out at a pH lower than the advantageous pH and to a white precipitate and thus to a loss of oxalic acid. Likewise, actual lower purities could have occurred, leading to a deficiency of oxalic acid after addition of the calculated amount of alkali metal base, which would in turn have led to the precipitation of silver oxalate (see above, step (b)) being carried out at a pH higher than the advantageous pH and to a grey-brown precipitate and thus likewise to a loss of valuable silver in the form of silver hydroxide/silver oxide.

Furthermore, the process of the invention makes it possible to dispense with high-purity oxalic acid as starting material, since it is, as described above, designed to compensate purity fluctuations in the oxalic acid starting material. The process of the invention is therefore very advantageous compared to commercial processes for producing supported silver catalysts on a large scale.

Step (a)

In step (a), oxalic acid is reacted with an alkali metal base in a solvent.

As solvent, it is in principle possible to use any solvent or any solvent mixture in which oxalic acid can be reacted with the alkali metal base to the second equivalence point of oxalic acid. Preference is given to using water or a mixture of water with at least one further suitable solvent as solvent. Particular preference is given to using water as sole solvent in (a).

According to the invention, the oxalic acid (ethanedioic acid) can in principle be used in any suitable form in (a). For example, the oxalic acid can be used as anhydrous oxalic acid or as oxalic acid dihydrate or as a mixture of anhydrous oxalic acid and oxalic acid dihydrate. Preference is given to using the oxalic acid as oxalic acid dihydrate in (a).

The concentration of oxalic acid in the solvent in (a) is in principle not subject to any particular restrictions as long as it is ensured that the second equivalence point can be determined. The solution of oxalic acid in the solvent preferably has an oxalic acid concentration in the range from 1 to 20% by weight, more preferably from 5 to 15% by weight, more preferably from 7 to 13% by weight, more preferably from 9 to 11% by weight.

As regards the alkali metal base used in (a), it is possible to use either a single alkali metal base or a mixture of two or more alkali metal bases. It is possible to use all bases which allow determination of the second equivalence point. In principle, weak or strong alkali metal bases can be used, with preference being given to using strong alkali metal bases. Particular preference is given to using alkali metal hydroxides, particularly preferably a single alkali metal hydroxide, as alkali metal base. Sodium hydroxide and potassium hydroxide are more particularly preferred, with potassium hydroxide being very particularly preferably used.

The alkali metal base used in (a) is preferably used as an aqueous solution. The concentration of this aqueous solution is in principle not subject to any particular restrictions. Preference is given to using an aqueous solution in which the concentration of the alkali metal base is in the range from 20 to 60% by weight, more preferably in the range from 30 to 55% by weight, more preferably in the range from 40 to 50% by weight, more preferably in the range from 45 to 50% by weight.

The determination of the second equivalence point of oxalic acid can be carried out by all conceivable methods or by a combination of two or more methods. The second equivalence point is preferably determined by means of a suitable color indicator and/or by measuring the pH of the solution resulting from mixing of the oxalic acid solution with the alkali metal base by means of a pH meter. Here, it is possible to use all pH meters which allow sufficiently precise measurements in the pH range of interest. Mention may be made of, for example, glass electrodes, hydrogen electrodes or ion-selective field effect transistors (ISFET). According to the invention preference is given to, inter alia, a glass electrode in which a half cell reaction generates an electric potential at the glass membrane which is directly related to the proton concentration, with the potential difference relative to the reference electrode producing a voltage which is largely linearly related to the pH; here, a silver-silver chloride half cell in most cases serves as reference electrode and together with the glass electrode forms a combination electrode. As regards preferred color indicators, mention may be made by way of example of phenolphthalein solutions, particularly preferably ethanolic phenolphthalein solutions. These phenolphthalein solutions more preferably have a concentration in the range from 0.05 to 1% by weight, more preferably from 0.1 to 0.5% by weight, more preferably from 0.15 to 0.3% by weight.

The expression "to the second equivalence point of oxalic acid" as used in the context of the present invention, in particular in step (a), refers to a process in which alkali metal base is added until the second equivalence point of oxalic acid is indicated via the pH of the preferably aqueous solution in the range from 8.5 to 8.7 by the method selected in each case for determining the attainment of the second equivalence point of oxalic acid. Step (a) of the process of the invention could, for the preferred embodiment in which the solvent used in (a) is water, also be formulated as (a) reacting oxalic acid with an alkali metal base in water as solvent to give alkali metal oxalate until the pH of the aqueous solution has reached a value in the range from 8.5 to 8.7.

As regards one of the abovementioned combinations of two or more methods of determining the second equivalence point, it can be preferred according to the invention firstly to use a color indicator for rough identification of the second equivalence point and to carry out the precise identification by means of a pH meter. The present invention therefore also provides the above-described process in which the second equivalence point is determined in (a) by means of a combination of at least one color indicator and a pH meter. Here, it is possible, for example, to use a first method, for example the use of a color indicator which indicates a pH of less than 8.5 for roughly determining the pH of the preferably aqueous solution. After this pH of less than 8.5, for example a pH in the range from 8.0 to less than 8.5, has been reached, a second method, for example the use of a pH meter, can be used for the fine determination.

As indicated above, the process of the invention offers the advantage of being able to react to quality fluctuations in the starting material oxalic acid. Since these fluctuations, especially in respect of the concentration of oxalic acid solutions to be used, are restricted to a particular range, it is possible according to the invention, in (a), firstly to add a particular amount of alkali metal base in a first step without having to monitor whether the second equivalence point has or has not been reached. Since the abovementioned concentration fluctuations of oxalic acid are in the range of not more than plus/minus 5% by weight, preferably not more than plus/minus 1.5% by weight, based on the concentration indicated for commercially available oxalic acid solutions, preference is given according to the invention to reacting the oxalic acid with up to 98.5%, preferably from 90 to 98.5%, of the equimolar amount, based on oxalic acid, of alkali metal base in aqueous solution in a first step (a1) in (a). The expression "the equimolar amount based on oxalic acid of alkali metal base" as used for the purposes of the invention refers, on the basis of x mol of oxalic acid, to an amount of monoacidic alkali metal base of 2x mol.

The present invention therefore provides the above-described process in which (a) comprises:

(a1) reacting the oxalic acid with up to 98.5%, preferably from 90 to 98.5%, of the equimolar amount based on oxalic acid of alkali metal base in aqueous solution.

According to the invention, the at least one method of determining the second equivalence point is preferably employed after the reaction according to (a1). If two or more methods are employed, it is possible, for example, to use a color indicator, for example for rough monitoring, in (a1) and subsequently use a pH meter for precise determination of the second equivalence point. It is likewise possible to carry out step (a1) without use of such a method of determination. In this case, the determination of the second equivalence point can, for example, be carried out by means of a pH meter, or a combination of color indicator and pH meter can be used, subsequent to step (a1).

As indicated above, the preferred concentration of the alkali metal base in the solution which is preferably used in (a) is in the range from 20 to 60% by weight, more preferably in the range from 30 to 55% by weight, more preferably in the range from 40 to 50% by weight, more preferably in the range from 45 to 50% by weight. This concentration is also preferably used when step (a1) is firstly carried out. To determine the second equivalence point precisely after (a1) with further addition of alkali metal base, it can be advantageous according to the invention to use solutions whose alkali metal base concentration is lower than that of the solution used in step (a1). For example, preference is given to using solutions whose alkali metal base concentration is in the range from 5 to 40% by weight, more preferably in the range from 10 to 30% by weight, more preferably in the range from 10 to 25% by weight, with the concentration being lower than the concentration used in step (a1).

In a preferred embodiment of the present invention, the aqueous solution obtained is brought after (a1) to a suitable temperature in order then to determine the second equivalence point precisely. This temperature is preferably in the range from 40 to 50° C., more preferably in the range from 40 to 45° C. The temperature of the solution is then preferably maintained during the determination of the second equivalence point.

Accordingly, the present invention provides the above-described process in which (a) comprises:
(a1) reacting oxalic acid with up to 98.5%, preferably from 90 to 98.5%, of the equimolar amount based on oxalic acid of alkali metal base in aqueous solution;
(a2) bringing the aqueous solution obtained according to (a1) to a temperature in the range from 40 to 50° C., preferably from 40 to 45° C.;
(a3) adding alkali metal base to the temperature-controlled aqueous solution according to (a2) to the second equivalence point of oxalic acid, with the aqueous solution being maintained at a temperature in the range from 40 to 50° C., preferably from 40 to 45° C., during the addition.

The present invention likewise provides the above-described process in which (a) comprises:
(a1) reacting oxalic acid with up to 98.5%, preferably from 90 to 98.5%, of the equimolar amount based on oxalic acid of alkali metal base in aqueous solution, with the alkali metal base being added as an aqueous solution whose concentration based on the alkali metal base is in the range from 20 to 60% by weight, preferably in the range from 30 to 55% by weight, more preferably in the range from 40 to 50% by weight, more preferably in the range from 45 to 50% by weight;
(a2) bringing the aqueous solution to a temperature in the range from 40 to 50° C., preferably from 40 to 45° C.;
(a3) adding alkali metal base to the temperature-controlled aqueous solution according to (a2) to the second equivalence point of oxalic acid, with the aqueous solution being maintained at a temperature in the range from 40 to 50° C., preferably from 40 to 45° C., during the addition and the alkali metal base being added as an aqueous solution whose concentration based on the alkali metal base is in the range from 5 to 40% by weight, preferably in the range from 10 to 30% by weight, more preferably in the range from 10 to 25% by weight, with the concentration being lower than the concentration used in step (a1).

Furthermore, it is possible, according to the invention, to reduce the concentration of the added aqueous alkali metal solution further in one or more further steps.

As regards the temperature control in (a2) and (a3), this can be achieved by measures known to those skilled in the art, preferably by determining the temperature of the aqueous solution directly in the aqueous solution in a suitable way and carrying out the required cooling and/or heating of the aqueous solution in a suitable way as a function of the temperature measured in the aqueous solution, for example by external cooling and/or external heating via, for example, a thermostated jacket of the reaction vessel used.

When the second equivalence point is reached, the addition of alkali metal base is stopped according to the invention. This rules out the possibility of an actual higher or actual lower purity compared to the indicated purity of the oxalic acid used leading to the use of too little or too much alkali metal base, which is possible in the case of a purely theoretical calculation of the alkali metal base required on the basis of the indicated purity of the oxalic acid. Especially in industrial-scale processes for producing the catalysts in question, this flexibility is of very great importance since it enables the fluctuations of the quality of the oxalic acid starting material to be countered without further difficulties and precise analysis of the oxalic acid batches used and accordingly the corresponding adaptation of the process for preparing alkali metal oxalate is dispensed with entirely.

Step (b)

In step (b), the alkali metal oxalate obtained at the second equivalence point according to step (a) is, according to the invention, reacted in a solvent, preferably water, with a silver salt to give silver oxalate.

The order of addition can generally be chosen freely. Preference is given to providing the silver salt in the solvent, preferably water, and adding the aqueous solution comprising the alkali metal oxalate obtained according to (a), for example preferably (a3). The reaction mixture formed by the addition is preferably stirred continually or periodically in a suitable way during the addition.

The temperature of the reaction mixture formed by the reaction is preferably kept constant in the range from 40 to 50° C., preferably in the range from 40 to 45° C. As regards keeping the temperature constant, this can be achieved by means of measures known to those skilled in the art, with the temperature of the aqueous solution preferably being determined in a suitable way directly in the aqueous solution and the required cooling and/or heating of the aqueous solution being carried out in a suitable way as a function of the temperature measured in the aqueous solution, for example by external cooling and/or external heating via, for example, a thermostated jacket of the reaction vessel used.

While the silver salt used in (b) can in principle be chosen freely, preference is given to using a silver salt which is at least partially, preferably completely, soluble in water, preferably at the abovementioned temperatures, or a mixture of two or more such silver salts as silver salt. Preference is given to using silver nitrate as silver salt. The aqueous solution of the silver salt which is preferably used according to the invention preferably has a concentration of silver salt in the range from 15 to 40% by weight, more preferably from 20 to 35% by weight, more preferably from 25 to 30% by weight.

According to the invention, the reaction of the alkali metal oxalate with the silver salt in a step (b1) is preferably followed by a step (b2) in which the silver oxalate formed by the reaction is separated off from the suspension obtained according to (b1). This separation is not subject to any particular restrictions and is preferably carried out as a filtration.

According to the invention, the silver oxalate which has been separated off is preferably washed with deionized water in order to reduce the content of impurities in the silver oxalate. The silver oxalate is particularly preferably washed until the washings have a conductivity of not more than 60 microsiemens/cm, preferably not more than 50 microsiemens/cm, more preferably not more than 40 microsiemens/cm, in each case preferably determined by electrochemical resistance measurement, for example preferably by means of a conductivity measuring instrument from WTW, model LF 323, electrode Tetra Con 325.

After the last washing operation, the silver oxalate which has been separated off is treated by means of the separation process, for example preferably the filtration, until no more water is released by the silver oxalate. According to the invention, it is not necessary to continue this concentration operation until the silver oxalate which ultimately results has only a very low water content. Rather, it has been found that residual moisture contents determined by means of a moisture measuring instrument such as preferably a Mettler Toledo HB43 IR dryer in the range from 10 to 25% by weight, preferably from 15 to 25% by weight, are satisfactory for passing the silver oxalate to step (c).

Accordingly, the present invention provides the above-described process in which (b) comprises:
(b1) adding the aqueous solution obtained according to (a3) to an aqueous solution of the silver salt having a temperature in the range from 40 to 50° C., preferably from 40 to 45° C., to give a suspension comprising the silver oxalate;
(b2) separating the silver oxalate from the suspension and washing of the silver oxalate which has been separated off with deionized water as washing water until the washings have an electrical conductivity of not more than 60 microsiemens/cm;
(b3) concentrating the silver oxalate, preferably to a residual moisture content of the silver oxalate in the range from 10 to 25% by weight, based on silver oxalate.

Unlike in processes described in the prior art, it is thus not necessary in the process of the invention to separate off and concentrate two different precipitates (silver hydroxide and silver oxalate) before addition of ethylenediamine to the silver oxalate. Rather, simple concentration of silver oxalate as described in step (b3) is sufficient due to the choice of the starting materials.

The silver oxalate which can be obtained from (b), preferably from (b3), is according to the invention reacted with a diamine compound in a solvent, preferably water, in step (c) to give a diamine-silver oxalate complex.

Step (c)

The diamine compound used in step (c) is in principle not subject to any particular restrictions as long as it is ensured that a diamine-silver oxalate complex is formed. Diamine compounds having from 1 to 6 carbon atoms are preferred. Diamine compounds having from 2 to 5 carbon atoms are particularly preferred. Very particular preference is given to alkylenediamines having from 2 to 5 carbon atoms, with further preference being given to ethylenediamine (1,2-ethanediamine) and propylenediamine (1,3-propanediamine). Ethylenediamine is particularly preferred.

According to the invention, preference is given to initially charging the diamine compound as aqueous solution and adding the silver oxalate as described above in step (c). Here, the aqueous solution of the diamine compound which is preferably used has a concentration of the diamine compound in the range from 45 to 70% by weight, more preferably from 50 to 65% by weight, more preferably from 50 to 60% by weight.

The complexation according to step (c) is preferably carried out at temperatures of up to 35° C., more preferably at temperatures of up to 30° C. The temperature of the reaction mixture present in the reaction according to (c) is very particularly preferably set to values in the range from 10 to 33° C., more preferably in the range from 15 to 30° C.

According to the invention, a solution having a silver content, calculated as elemental silver, in the range from 25 to 35% by weight, based on the total weight of the solution, is preferably obtained in (c). Silver contents in the range from 25 to 32% by weight or from 28 to 30% by weight are more preferred. The present invention therefore provides the above-described process in which the solution obtained according to (c) has a silver content, calculated as elemental silver, in the range from 25 to 32% by weight, based on the total weight of the solution.

It is in principle possible to use the solution resulting from (c) as such in order to produce a supported silver catalyst in a suitable way. For example, it is possible to apply the solution to a suitable porous support material, for example preferably by impregnation. According to the invention, supports which are impregnated therewith and have a silver content, calculated as elemental silver, in the range from 1 to 50% by weight, preferably in the range from 5 to 35% by weight and more preferably in the range from 10 to 25% by weight, in each case based on the weight of the support calcined according to the invention, can be produced.

In a preferred embodiment of the process of the invention, an impregnated support which comprises at least one promoter in addition to silver is provided by impregnation of the porous support material. Preferred promoters are, for example, rhenium, tungsten, lithium, cesium and sulfur. In principle, each of these promoters can be applied separately from silver to the support having a suitable form. It is conceivable for, for example, each promoter to be applied in a separate impregnation step or two or more promoters to be applied in a separate impregnation step in each case. A drying step and/or a calcination step can in principle be carried out between the individual impregnation steps.

However, particular preference is given, for the purposes of the present invention, to applying the promoter or promoters to the support together with the silver in a single step (d) by impregnating the porous support material with an aqueous solution comprising a compound comprising the promoter or compounds comprising promoters in addition to the silver-comprising compound.

Step (d)

Accordingly, the present invention provides the above-described process which additionally comprises
(d) adding at least one promoter to the solution obtained according to (c).

The process of the invention therefore also comprises impregnating the unimpregnated porous support material in a single step by means of a single aqueous solution comprising both silver and all promoters, in particular rhenium, tungsten, lithium, cesium and optionally sulfur, which the catalyst ultimately obtained is to comprise. Since the unimpregnated porous support material is impregnated in this single step both with silver and with the promoters, any intermediate treatments such as drying or calcination which may be necessary in processes having a plurality of impregnation steps can be dispensed with.

If the promoter in (d) is rhenium, a halide, an oxyhalide, an oxide, an acid or a salt of a heteropolyacid of rhenium, for example a rhenate or perrhenate, is preferably used as rhenium-comprising compound in (d), optionally in the form of an aqueous solution. The rhenium-comprising compound is preferably a compound selected from the group consisting of ammonium perrhenate, rhenium(III) chloride, rhenium(V) chloride, rhenium(V) fluoride, rhenium(VI) oxide and rhenium(VII) oxide. Particular preference is given to ammonium perrhenate. The concentration of the aqueous solution of the rhenium-comprising compound is preferably in the range from 1 to 5% by weight, more preferably in the range from 2 to 4.5% by weight and more preferably in the range from 2.8 to 4.2% by weight of rhenium, in each case calculated as element. The impregnation according to the invention preferably produces an impregnated support whose rhenium content, calculated as elemental Re, is in the range from 50 to 1200 ppm by weight, more preferably from 100 to 1000 ppm by weight, more preferably in the range from 150 to 600 ppm by weight and more preferably in the range from 200 to 500 ppm by weight, in each case based on the weight of the calcined support.

If the promoter in (d) is tungsten, preferably in addition to rhenium, a tungsten salt or tungstic acid is preferably used as tungsten-comprising compound in (d), optionally in the form of an aqueous solution. Particular preference is given to tungstic acid. The concentration of the aqueous solution of the tungsten-comprising compound is preferably in the range from 0.1% by weight to 5% by weight, more preferably in the range from 0.5% by weight to 3% by weight and more preferably in the range from 0.8% by weight to 2.5% by weight, of tungsten, in each case calculated as element. The impregnation according to the invention preferably produces an impregnated support whose tungsten content, calculated as elemental W, is in the range from 10 to 800 ppm by weight, more preferably in the range from 20 to 500 ppm by weight, preferably in the range from 50 to 300 ppm by weight and more preferably in the range from 80 to 250 ppm by weight, in each case based on the weight of the calcined support.

If the promoter in (d) is lithium, preferably in addition to rhenium and tungsten, an at least partially water-soluble lithium salt is preferably used as lithium-comprising compound, optionally in the form of an aqueous solution. Particular preference is given to lithium nitrate. The concentration of the aqueous solution of the lithium-comprising compound is preferably in the range from 0.5 to 5% by weight, more preferably in the range from 1 to 4% by weight and more preferably in the range from 1.5 to 3% by weight, of lithium, calculated as element. The impregnation according to the invention preferably produces an impregnated support whose lithium content, calculated as elemental Li, is in the range from 50 to 700 ppm by weight, more preferably in the range from 75 to 400 ppm by weight and more preferably in the range from 100 to 250 ppm by weight, in each case based on the weight of the calcined support.

If the promoter in (d) is cesium, preferably in addition to rhenium and tungsten and lithium, an at least partially water-soluble cesium salt is preferably used as cesium-comprising compound, optionally in the form of an aqueous solution. Particular preference is given to cesium hydroxide. The concentration of the aqueous solution of the cesium-comprising compound is preferably in the range from 0.5 to 6% by weight, more preferably in the range from 1.5 to 5.5% by weight and more preferably in the range from 3 to 5% by weight, of cesium, calculated as element. The impregnation according to the invention preferably produces an impregnated support whose cesium content, calculated as elemental Cs, is in the range from 50 to 1500 ppm by weight, more preferably in the range from 100 to 800 ppm by weight, more preferably in the range from 200 to 700 ppm by weight and more preferably in the range from 250 to 600 ppm by weight, in each case based on the weight of the calcined support.

If the promoter in (d) is sulfur, preferably in addition to rhenium and tungsten and lithium and cesium, ammonium sulfate is preferably used as sulfur-comprising compound, optionally in the form of an aqueous solution. The concentration of the aqueous solution of the sulfur-comprising compound is preferably in the range from 0.05 to 0.5% by weight, more preferably in the range from 0.1 to 0.35% by weight and more preferably in the range from 0.15 to 0.3% by weight, of sulfur, calculated as element. The impregnation according to the invention preferably produces an impregnated support whose sulfur content, calculated as elemental S, is in the range from 0 to 100 ppm by weight, more preferably in the range from 2 to 100 ppm by weight, more preferably in the range from 1 to 50 ppm by weight, preferably in the range from 2 to 30 ppm by weight and more preferably in the range from 5 to 20 ppm by weight, in each case based on the weight of the support which has been calcined according to the invention.

Accordingly, the present invention provides the above-described process in which lithium, cesium, tungsten, rhenium and sulfur are added as promoters and the solution obtained according to (d) has a lithium content in the range from 50 to 700 ppm by weight, a cesium content in the range from 50 to 1500 ppm by weight, a tungsten content in the range from 10 to 800 ppm by weight, a rhenium content in the range from 50 to 1200 ppm by weight and a sulfur content in the range from 2 to 100 ppm by weight.

In a preferred embodiment of the process of the invention, the impregnation solution is produced from a preferably aqueous solution comprising tungsten and cesium, a preferably aqueous solution comprising lithium and sulfur and a preferably aqueous solution comprising rhenium. These three solutions comprise the promoters mentioned in such amounts that mixing of the three solutions in (d) with the solution obtained according to (c) gives an impregnation solution which comprises the promoters in the abovementioned amounts and allows the production of impregnated, calcined supports having the abovementioned preferred promoter contents.

As indicated above, a porous support material is preferably treated by impregnation with the preferably aqueous solution obtained according to (c) or according to (d) in order to produce the supported silver catalyst of the invention. For this purpose, a porous support material is preferably firstly provided in a step (e).

This porous support material preferably comprises from 90 to 99% by weight, more preferably from 92 to 98% by weight, more preferably from 95 to 97% by weight, based on the total weight of the porous support material, of aluminum oxide, calculated as $Al_2O_3$.

While all suitable aluminum oxide phases, for example, inter alia, alpha-aluminum oxide, gamma-aluminum oxide or theta-aluminum oxide or aluminum oxide mixed phases, are conceivable in principle, alpha-aluminum oxide is particularly preferred for the purposes of the present invention. More preferably, at least 98% by weight, more preferably at least 98.5% by weight, more preferably at least 99% by weight, more preferably at least 99.9% by weight, of the aluminum oxide comprised in the porous support material is alpha-aluminum oxide.

The present invention therefore provides the above-described process which additionally comprises
(e) providing a porous support material which preferably comprises alpha-aluminum oxide, more preferably at least 98% by weight of alpha-aluminum oxide;
(f) impregnating the porous support material with the solution obtained according to (c) or (d).

In a further preferred embodiment, the porous support material comprises at least one alkali metal, with the total alkali metal content of the unimpregnated support preferably being in the range up to 2500 ppm, preferably from 10 to 2500 ppm, more preferably from 50 to 1000 ppm, in each case based on the total weight of the unimpregnated support and calculated as element. The porous support material particularly preferably comprises sodium and/or potassium, more preferably sodium and potassium. If the porous support material comprises sodium, the sodium content is preferably in the range from 10 to 1500 ppm, more preferably from 10 to 800 ppm, more preferably from 10 to 600 ppm, more preferably from 10 to 500 ppm, based on the total weight of the porous support material and calculated as Na. If the porous support material comprises potassium, the potassium content is preferably not more than 1000 ppm, more preferably not more than 500 ppm, more preferably not more than 200 ppm, for example in the range from 10 to 200 ppm, based on the total weight of the porous support material and calculated as K.

In a further preferred embodiment, the porous support material comprises at least one alkaline earth metal, with the total alkaline earth metal content of the porous support material preferably being up to 2500 ppm, for example in the range from 1 to 2500 ppm, more preferably from 10 to 1200 ppm, more preferably from 100 to 800 ppm, in each case based on the total weight of the porous support material and calculated as element. The porous support material particularly preferably comprises calcium and/or magnesium, more preferably calcium and magnesium. If the porous support material comprises calcium, the calcium content is preferably in the range from 10 to 1500 ppm, more preferably from 20 to 1000 ppm, more preferably from 30 to 600 ppm, in each case based on the total weight of the porous support material and calculated as Ca. If the porous support material comprises magnesium, the magnesium content is preferably in the range up to 800 ppm, preferably from 1 to 500 ppm, more preferably from 1 to 250 ppm, more preferably from 1 to 100 ppm, in each case based on the total weight of the porous support material and calculated as Mg.

In a preferred embodiment, the porous support material comprises silicon in an amount in the range from 50 to 10 000 ppm, preferably from 100 to 5000 ppm, more preferably from 100 to 2500 ppm, in each case based on the total weight of the porous support material and calculated as Si.

In an embodiment, the porous support material comprises zinc in an amount in the range from 10 to 1500 ppm, preferably from 10 to 750 ppm, more preferably from 10 to 300 ppm, in each case based on the total weight of the porous support material and calculated as Zn.

In an embodiment, the porous support material comprises zirconium in an amount in the range from 1 to 10 000 ppm, preferably from 10 to 8000 ppm, more preferably from 10 to 6000 ppm, more preferably from 10 to 5000 ppm, in each case based on the total weight of the porous support material and calculated as Zr.

In an embodiment, the porous support material comprises both zinc in an amount in the range from 10 to 1500 ppm, preferably from 10 to 750 ppm, more preferably from 10 to 300 ppm, and zirconium in an amount in the range from 1 to 10 000 ppm, preferably from 10 to 8000 ppm, more preferably from 10 to 6000 ppm, more preferably from 10 to 5000 ppm, in each case based on the total weight of the porous support material and calculated as Zn or Zr.

In another embodiment, the porous support material comprises less than 10 ppm of zinc and less than 1 ppm of zirconium, with preference being given in this embodiment to the porous support material comprising both zinc and zirconium in an amount below the respective detection limit or being both zinc- and zirconium-free.

In a preferred embodiment of the present invention, the porous support material has a BET surface area determined in accordance with DIN ISO 9277 in the range from 0.1 to 5 m$^2$/g, more preferably in the range from 0.2 to 2 m$^2$/g, more preferably in the range from 0.3 to 1.5 m$^2$/g, more preferably in the range from 0.4 to 1.4 m$^2$/g, more preferably from 0.5 to 1.3 m$^2$/g, more preferably in the range from 0.6 to 1.2 m$^2$/g and particularly preferably in the range from 0.7 to 1.0 m$^2$/g.

In a preferred embodiment of the present invention, the porous support material has pores having diameters in the range from 0.1 to 100 microns, with the pore distribution preferably being monomodal or polymodal, more preferably polymodal, particularly preferably bimodal. In the particularly preferred bimodal pore distribution, the peak maxima obtained by determining the pore diameter by mercury (Hg) porosimetry in accordance with DIN 66133 are more preferably in the range from 0.1 to 10 microns and from 15 to 100 microns, preferably in the range from 0.1 to 5 microns and from 17 to 80 microns, more preferably in the range from 0.1 to 3 microns and from 20 to 70 microns, more preferably in the range from 0.1 to 2.5 microns and from 20 to 65 microns.

The geometric shape of the porous support material used according to the invention can in principle be selected freely and can in principle be matched to the specific requirements which the catalyst has to meet during use, in particular in the gas-phase oxidation of ethene to ethylene oxide. The porous support material advantageously has a geometry which allows unhindered diffusion of the reaction gases used and occurring in this reaction to a very large part of the catalytically active external and internal surface area of the support material which is coated with silver particles and optionally with further promoters.

In a preferred embodiment, the porous support material has the geometry of an extrudate, for example a hollow extrudate, a star, a sphere, a ring or cylinder. According to the invention, preference is given to using a support material having the geometry of a cylinder. Further preference is given to a support material which has the geometry of a cylinder having a height in the range from 5 to 10 mm, an external diameter in the range from 5 to 10 mm and a ratio of external diameter/mm to wall thickness/mm in the range from 2.5 to 4.5. Very particular preference is given to cylinders having the following geometries (external diameter×length×internal diameter, in each case in mm): 5×5×2, 6×6×3, 7×7×3, 8×8×3, 8×8.5×3, 8×8.5×3.5, 8.5×8×3.5, 8.5×8×3, 9×9×3, 9.5×9×3, 9.5×9×3.5. Each of the lengths indicated comprises tolerances in the region of plus/minus 0.5 mm.

Step (g)

Step (f) can be followed by at least one after-treatment step, for example a drying step, e.g. one, two or more drying steps. Drying is usually carried out at temperatures in the range from 2 to 200° C. The after-treatment step is preferably drying by means of vacuum treatment, as described above. This evacuation is preferably carried out to a pressure in the range up to 500 mbar, more preferably to a pressure of not more than 250 mbar and particularly preferably to a pressure of not more than 30 mbar. The vacuum treatment is preferably carried out at a temperature in the range from 2° C. to 50° C., more preferably at a temperature in the range from 5° C. to 30° C. and particularly preferably at room temperature. The vacuum treatment is carried out for a time of at least 1 minute, preferably at least 5 minutes, more preferably for a time in the range from 5 minutes to 120 minutes, in particular in the range from 10 minutes to 45 minutes, particularly preferably in the range from 10 minutes to 20 minutes.

Accordingly, the present invention also provides a process as described above which comprises drying of the support material impregnated according to (f).

The support material impregnated according to (f) is, optionally after drying, preferably calcined. Calcination is preferably carried out at temperatures in the range from 150 to 750° C., preferably in the range from 200 to 500° C., more preferably in the range from 220 to 350° C., more preferably in the range from 250 to less than 300° C. and particularly preferably in the range from 270 to 295° C., with the calcination time generally being at least 5 minutes or more, for example in the range from 5 minutes to 24 hours or in the range from 10 minutes to 12 hours. The calcination time is particularly preferably in the range from 5 minutes to 3 hours. The calcination can be carried out at a constant temperature, but embodiments in which the temperature is changed continuously or discontinuously during the calcination time are also comprised.

The calcination can be carried out under any gas atmosphere suitable for this purpose, for example in an inert gas or a mixture of an inert gas and from 10 ppm to 21% by volume of oxygen. Examples of inert gases are nitrogen, argon, carbon dioxide, helium and combinations of the abovementioned inert gases. If the calcination is carried out under an inert gas, nitrogen is particularly preferred. In an alternative preferred embodiment, air and/or lean air is used.

Furthermore, the calcination is preferably carried out in a muffle furnace, convection furnace, in a rotary tube furnace and/or a belt calcination furnace.

Accordingly, the present invention provides the process as described above which additionally comprises
(g) calcining the impregnated and subsequently optionally dried support material obtained according to (f), preferably at a temperature in the range from 270 to 295° C.

Preferred Calcination

In a preferred embodiment of the present invention, the impregnated support material which has been obtained according to (f) and has a temperature $T_0$ is calcined according to (g), wherein (g) comprises:
(g1) heating the impregnated support material from the temperature $T_0$ to a temperature $T_1$ at a heating rate of at least 30 K/min, preferably in the range from 30 to 80 K/min, more preferably in the range from 40 to 75 K/min;
(g2) holding the support material which has been heated to the temperature $T_1$ at a temperature $T_2$, where $T_2$ is preferably in the range from 0.95 $T_1$ to 1.1 $T_1$;
(g3) cooling the support material which has been held at the temperature $T_2$ to a temperature $T_3$, where $T_3$ is not more than 60° C.

Should the impregnated support material be obtained at a temperature greater than $T_0$ after the impregnation, in particular after the particularly preferred single-step impregnation, it is, according to the invention, firstly cooled to the temperature $T_0$.

In principle, temperatures $T_0$ in the range up to 35° C., for example in the range up to 30° C., are conceivable. The temperature $T_0$ is preferably in the range from 5 to 20° C., more preferably in the range from 10 to 15° C.

In the preferred embodiments, the temperature $T_0$ ensures, according to the invention, that the support material obtained in step (f) does not have to be subjected to any predrying before it is, according to the invention, heated at a heating rate of at least 30 K/min in step (g1).

The present invention therefore preferably provides a process in which the catalyst obtained after impregnation of the support as described above is not exposed to a temperature greater than 35° C., preferably greater than 30° C., more preferably greater than 25° C. and more preferably greater than 20° C., before heating at a heating rate of at least 30 K/min.

Step (g1)

In step (g1) of the process of the invention, the impregnated support material provided at the temperature $T_0$ is heated at a heating rate of at least 30 K/min.

In principle, heating rates of up to 150 K/min, for example up to 100 K/min or up to 80 K/min, are conceivable. The heating rate in step (g1) is preferably in the range from 30 to 80 K/min, more preferably in the range from 40 to 75 K/min.

In step (g1) of the process of the invention, the support material is heated from the temperature $T_0$ to the temperature $T_1$.

According to the invention, heating is carried out to temperatures $T_1$ which are suitable for calcination of the impregnated support material. Here, temperatures $T_1$ of up to 350° C., for example up to 340° C. or up to 330° C. or up to 320° C. or up to 310° C. or up to 300° C., are conceivable in principle. Preferred minimum temperatures $T_1$ are in the region of 250° C. Accordingly, temperatures $T_1$ in the range from 250 to 310° C. or in the range from 250 to 300° C. are conceivable. However, it has been found according to the invention that it is possible to set calcination temperatures of less than 300° C. The present invention therefore provides the process as described above in which the temperature $T_1$ is less than 300° C., preferably less than or equal to 299° C.

According to the invention, the temperature $T_1$ is preferably in the range from 250 to 295° C., more preferably in the range from 260 to 295° C., more preferably in the range from 270 to 295° C., more preferably in the range from 270 to 290° C., for example in the range from 270 to 285° C., from 275 to 290° C. or from 275 to 285° C.

The way in which the heating rate according to the invention is achieved is in principle not subject to any restrictions. During heating, the support material present at the temperature $T_0$ is preferably brought into contact with a gas and the heating of the support material is more preferably effected by means of this gas; the gas thus has a temperature which allows the support material to be heated to the temperature $T_1$.

The chemical composition of the gas which is brought into contact with the support material in order to heat the support material is in principle not subject to any restrictions. Thus, it is, for example, conceivable for the gas to comprise oxygen, in which case possible oxygen contents of the gas are, for example, up to 100% by volume or up to 25% by volume. The use of air, for example, is also conceivable. Lower oxygen contents are also conceivable, with, for example, mixtures of nitrogen and air such as lean air being conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases whose oxygen content is preferably less than 10 ppm, more preferably in the range from 5 to 9 ppm, as gas for heating. Mention may be made by way of example of nitrogen, carbon dioxide, argon and/or helium as inert gases. Particular preference is given to using nitrogen as inert gas for the purposes of the present invention.

Accordingly, the present invention provides the process as described above in which the heating in (g1) is effected by bringing the support material into contact with an inert gas $I_1$.

The present invention preferably provides the process as described above in which the heating in (g1) is effected by bringing the support material into contact with an inert gas $I_1$ comprising less than 10 ppm, preferably from 5 to 9 ppm, of oxygen.

The present invention more preferably provides the process as described above in which the heating in (g1) is effected by bringing the support material into contact with an inert gas $I_1$ which is nitrogen and comprises less than 10 ppm, preferably from 5 to 9 ppm, of oxygen.

The expression "inert gas $I_1$ comprising less than 10 ppm, preferably from 5 to 9 ppm, of oxygen" refers to a gas mixture consisting of the inert gas $I_1$ and oxygen, with the oxygen content of less than 10 ppm or from 5 to 9 ppm relating to the oxygen content of the gas mixture and the inert gas $I_1$ being able to be a mixture of 2 or more inert gases.

For the purposes of the present invention, very particular preference is given to using technical-grade nitrogen, preferably obtained from fractionation of air, which typically comprises nitrogen in the range from 99.995 to 99.9999, oxygen in the range from 6 to 8 ppm and traces of noble gases as gas with which the support material is brought into contact during heating in step (g1).

The temperature of the gas with which the support material is brought into contact in the heating step is basically selected so that the heating rates according to the invention are made possible and the support material can be brought to the temperature $T_1$. The gas with which the support material is brought into contact during the heating in step (g1) preferably has a temperature in the range from $T_1$ to 1.1 $T_1$, more preferably in the range from $T_1$ to 1.07 $T_1$, more preferably in the range from $T_1$ to 1.05 $T_1$.

The contacting of the support material with the gas in step (g1) can in principle be carried out in any way as long it is ensured that the heating rate according to the invention of the support material is achieved. In this respect, the support material is particularly preferably brought into contact with a stream of the gas, preferably with a stream of the inert gas $I_1$, i.e. the gas flows through the support material. Here, the volume flow of the gas is basically selected so that the heating rate according to the invention is achieved. In particular, the volume flow of the gas is selected so that the heating rate according to the invention is achieved by the combination of the temperature and volume flow of the gas which is brought into contact with the support material. The volume flow is particularly preferably in the range from 2500 to 5000 m³/h, in particular in the range from 3200 to 4500 m³/h.

In a preferred embodiment, the present invention provides the process as described above in which an inert gas $I_1$, preferably nitrogen, which preferably comprises less than 10 ppm, more preferably from 5 to 9 ppm, of oxygen and preferably has a temperature in the range from $T_1$ to 1.1 $T_1$, flows through the support material to be heated according to (g1) at a volume flow in the range from 2500 to 5000 m³/h, more preferably from 3200 to 4500 m³/h.

In the heating of the support material according to step (g1), the heating can be constant or vary as long as it is ensured that the overall heating rate calculated as the temperature difference $(T_1-T_0)$ divided by the time necessary for the total heating is at least 30 K/min, preferably in the range from 30 to 80 K/min, more preferably in the range from 30 to 75 K/min, more preferably in the range from 30 to 70 K/min. The heating rate over the entire heating operation is preferably at least 30 K/min, more preferably in the range from 30 to 80 K/min, more preferably in the range from 30 to 75 K/min, more preferably in the range from 30 to 70 K/min.

Ranges for the heating rate which are possible according to the invention are, for example, from 35 to 80 K/min or from 40 to 75 K/min or from 40 to 70 K/min or from 45 to 70 K/min or from 50 to 70 K/min or from 55 to 70 K/min or from 60 to 70 K/min or from 65 to 70 K/min.

Step (g2)

In a preferred embodiment, the support material which has been heated to the temperature $T_1$ is maintained at a temperature $T_2$ which is suitable for the purposes of the calcination according to the invention after heating, preferably directly after heating. Preference is given here to temperatures $T_2$ which are in the region of the temperature $T_1$. Particular preference is given to temperatures $T_2$ which are in the range from 0.95 to 1.1 $T_1$, for example in the range from 0.95 to 1.05 $T_1$, from 0.96 to 1.04 $T_1$, from 0.97 to 1.03 $T_1$, from 0.98 to 1.02 $T_1$ or from 0.99 to 1.01 $T_1$. The temperature $T_2$ is preferably selected so as to be less than 300° C., preferably less than or equal to 299° C.

The holding of the support material at the temperature $T_2$ also comprises embodiments in which the value of $T_2$ is not constant during the hold time but varies within the above-described limits. The present invention thus also comprises, inter alia, embodiments in which the support material is held at two or more different temperatures which are within the above-described limits for $T_2$.

The duration of the holding of the support material at the temperature $T_2$ is in principle not subject to any restrictions. For the purposes of the present invention, the support is preferably maintained at the temperature $T_2$ for a time in the range from 1 to 15 minutes, preferably from 2 to 10 minutes, more preferably from 3 to 5 minutes, in (g2).

The way in which the holding at temperature according to the invention in step (g2) is achieved is in principle not subject to any restrictions. During the holding at the temperature $T_2$, the support material is preferably brought into contact with a gas having a temperature which allows the support material to be maintained at the temperature $T_2$.

The chemical composition of the gas which is brought into contact with the support material in order to hold the support material at the temperature $T_2$ is in principle not subject to any restrictions. It is conceivable, for example, for the gas to comprise oxygen and have, for example, an oxygen content of up to 100% by volume or up to 25% by volume. Thus, for example, the use of air is conceivable. Lower contents of oxygen are also conceivable, and mixtures of nitrogen and air such as lean air are, for example, conceivable. Mention may be made of oxygen contents of the gas of up to 20% by volume or up to 15% by volume or up to 10% by volume or up to 5% by volume or up to 1% by volume. For the purposes of the present invention, particular preference is given to using an inert gas or a mixture of two or more inert gases having an oxygen content of preferably less than 10 ppm, more preferably in the range from 5 to 9 ppm, as gas for the holding of the support material at the temperature $T_2$. As inert gases, mention may be made by way of example of nitrogen, carbon dioxide, argon and helium. Nitrogen is particularly preferably used as inert gas for the purposes of the present invention.

Accordingly, the present invention provides the process as described above in which the holding at temperature in (g2) is effected by bringing the support material into contact with an inert gas $I_2$.

The present invention preferably provides the process as described above in which the holding at temperature in (g2) is effected by bringing the support material into contact with an inert gas $I_2$ comprising less than 10 ppm, preferably from 5 to 9 ppm, of oxygen.

The present invention more preferably provides the process as described above in which the holding at temperature in (g2) is effected by bringing the support material into contact with an inert gas $I_2$ which is nitrogen and comprises less than 10 ppm, preferably from 5 to 9 ppm, of oxygen.

The expression "inert gas $I_2$ comprising less than 10 ppm, preferably from 5 to 9 ppm, of oxygen" refers to a gas mixture consisting of the inert gas $I_2$ and oxygen, with the oxygen content of less than 10 ppm or from 5 to 9 ppm relating to the oxygen content of the gas mixture and the inert gas $I_2$ being able to be a mixture of 2 or more inert gases.

For the purposes of the present invention, very particular preference is given to using technical-grade nitrogen, preferably obtained from fractionation of air, which typically comprises nitrogen in the range from 99.995 to 99.9999% by volume, oxygen in the range from 6 to 8 ppm and traces of noble gases as gas with which the support material is brought into contact in the holding at temperature in step (g2).

The present invention therefore provides the process as described above in which the holding temperature in (g2) is effected by means of an inert gas $I_2$, preferably by means of nitrogen, which preferably comprises less than 10 ppm, more preferably from 5 to 9 ppm, of oxygen.

The temperature of the gas with which the support material is brought into contact in the holding at temperature in (g2) is basically selected so that the hold temperature according to the invention is made possible. The gas with which the support material is brought into contact during the holding at temperature in step (g2) preferably has a temperature in the range from $T_2$ to $1.1\ T_2$, more preferably in the range from $T_2$ to $1.07\ T_2$, more preferably in the range from $T_2$ to $1.05\ T_2$, for example in the range from $T_2$ to $1.04\ T_2$ or in the range from $T_2$ to $1.03\ T_2$ or in the range from $T_2$ to $1.02\ T_2$ or in the range from $T_2$ to $1.01\ T_2$.

The contacting of the support material with the gas in step (g2) can in principle be carried out in any way as long it is ensured that the holding according to the invention of the support material at the temperature $T_2$ is achieved.

In this respect, the support material is particularly preferably brought into contact with a stream of the gas, preferably with a stream of the inert gas $I_2$, i.e. the gas flows through the support material. Here, the volume flow of the gas is basically selected so that the holding according to the invention of the support material at the temperature $T_2$ is achieved. In particular, the volume flow of the gas is selected so that the holding according to the invention of the support at the temperature $T_2$ is achieved by the combination of the temperature and the volume flow of the gas which is brought into contact with the support material. The volume flow is particularly preferably in the range from 1000 to 3000 m³/h, more preferably from 1500 to 2000 m³/h.

In a preferred embodiment, the present invention provides the process as described above in which an inert gas $I_2$, preferably nitrogen, flows through the support material to be maintained at the temperature $T_2$ according to (g2), with $I_2$ preferably comprising less than 10 ppm, more preferably from 5 to 9 ppm, of oxygen, $I_2$ preferably having a temperature in the range from $T_2$ to $1.05\ T_1$ and $I_2$ preferably flowing through the support at a volume flow in the range from 1000 to 3000 m³/h, more preferably from 1500 to 2000 m³/h.

For the purposes of the present invention, the inert gas $I_1$ is preferably, but not necessarily, used as inert gas $I_2$, with, as described above, the volume flow of $I_2$ being able to be different from the volume flow of $I_1$ and/or the temperature of $I_2$ being able to be different from the temperature of $I_1$.

Step (g3)

In a preferred embodiment, the support material which has been maintained at the temperature $T_2$ is cooled to a temperature $T_3$ after the holding at temperature, preferably directly after the holding at temperature. The value of $T_3$ is in principle not subject to any particular restrictions. For the purposes of the present invention, temperatures $T_3$ of not more than 60° C. are preferred.

The way in which the cooling according to the invention in step (g3) is achieved is in principle not subject to any restrictions. In the cooling to the temperature $T_3$, the support material is preferably brought into contact with a gas having a temperature which allows the support material to be cooled to the temperature $T_3$.

The chemical composition of the gas which is brought into contact with the support material to cool the support material to the temperature $T_3$ is in principle not subject to any restrictions. Thus, for example, it is conceivable to use an inert gas as is used, for example, in steps (g1) or (g2) as gas. For the purposes of the present invention, particular preference is given to using a gas having an oxygen content of at least 5% by volume, preferably at least 10% by volume, more preferably at least 15% by volume, more preferably at least 20% by volume, as gas for cooling to the temperature $T_3$. In particular, air is used according to the invention for cooling in (g3).

According to the invention, the support material is preferably cooled in step (g3) at a cooling rate in the range from 30 to 80 K/min, preferably in the range from 40 to 60 K/min, more preferably in the range from 45 to 55 K/min.

After step (g3), the calcined and cooled support material obtained in this way can either be used directly as catalyst or be stored in a suitable manner.

Belt Calciner

The configuration in terms of apparatus of the above-described calcination process is essentially not subject to any restrictions as long as it is ensured that the heating according to the invention according to (g1), preferably also the holding at temperature according to the invention according to (g2), preferably also the cooling according to the invention according to (g3) can be carried out as described above. According to the invention, preference is given to embodiments in which at least the heating according to (g1), preferably the heating according to (g1), and the holding at temperature according to (g2) and optionally also the cooling according to (g3) can be carried out continuously. The process of the invention is particularly preferably carried out continuously in a belt calciner at least in respect of the step (g1), preferably at least in respect of the steps (g1) and (g2).

Catalyst which is Obtained or Obtainable According to the Invention

It has surprisingly been found that the supported silver catalyst which can be obtained according to the invention and/or has been obtained according to the invention has advantageous properties as catalyst in the oxidation of ethene to ethylene oxide.

Accordingly, the present invention also provides a supported silver catalyst obtained or obtainable by a process comprising (a) reacting oxalic acid with an alkali metal base in a solvent, preferably water, to the second equivalence point of oxalic acid to give alkali metal oxalate;

(b) reacting the alkali metal oxalate obtained according to (a) with a silver salt in a solvent, preferably water, to give silver oxalate;

(c) forming a complex of the silver oxalate obtained according to (b) with a diamine compound in a solvent, preferably water, to give a diamine-silver oxalate complex;

(d) optionally adding at least one promoter to the solution obtained according to (c);

(e) providing a porous support material which preferably comprises alpha-aluminum oxide, more preferably at least 98% by weight of alpha-aluminum oxide, where the porous support material preferably has a cylindrical geometry and a cylinder preferably has a length in the range from 5 to 10 mm, an external diameter in the range from 5 to 10 mm and a ratio of external diameter/mm to wall thickness/mm in the range from 2.5 to 4.5;
(f) impregnating the porous support material with the solution obtained according to (c) or (d);
(g) calcining the impregnated support material obtained according to (f), preferably at a temperature in the range from 270 to 295° C.

In particular, the present invention provides this supported silver catalyst having a silver content in the range from 5 to 30% by weight, a lithium content in the range from 25 to 400 ppm by weight, a cesium content in the range from 25 to 750 ppm by weight, a tungsten content in the range from 5 to 500 ppm by weight, a rhenium content in the range from 25 to 600 ppm by weight and a sulfur content in the range from 0 to 50 ppm by weight applied to the porous support material by impregnation, in each case calculated as element and based on the total weight of the catalyst, where the porous support material has a cylindrical geometry and a cylinder preferably has a length in the range from 5 to 10 mm, an external diameter in the range from 5 to 10 mm and a ratio of external diameter/mm to wall thickness/mm in the range from 2.5 to 4.5.

According to the invention, it has surprisingly been found that the process of the invention comprising the steps (a), (b) and (c) gives a catalyst which has preferred properties in the preparation of ethylene oxide from ethene and oxygen. These properties are due to the specific steps (a), (b) and (c). The present invention therefore also provides a precursor of a supported silver catalyst obtained or obtainable by a process comprising
(a) reacting oxalic acid with an alkali metal base in a solvent, preferably water, to the second equivalence point of oxalic acid to give alkali metal oxalate;
(b) reacting the alkali metal oxalate obtained according to (a) with a silver salt in a solvent, preferably water, to give silver oxalate;
(c) forming a complex of the silver oxalate obtained according to (b) with a diamine compound in a solvent, preferably water, to give a diamine-silver oxalate complex;
(d) optionally adding at least one promoter to the solution obtained according to (c);
(e) provision of a porous support material which preferably comprises alpha-aluminum oxide, more preferably at least 98% by weight of alpha-aluminum oxide, where the porous support material preferably has a cylindrical geometry and a cylinder preferably has a length in the range from 5 to 10 mm, an external diameter in the range from 5 to 10 mm and a ratio of external diameter/mm to wall thickness/mm in the range from 2.5 to 4.5;
(f) impregnating the porous support material with the solution obtained according to (c) or (d) to give a precursor of a supported silver catalyst.

This precursor of a supported silver catalyst can be calcined as described above and subsequently be used as catalyst, for example for preparing ethylene oxide from ethene and oxygen. It is likewise possible to use this precursor directly in a suitable process, for example the preparation of ethylene oxide from ethene and oxygen, and carry out the calcination of the precursor to give the catalyst in the reactor used for this epoxidation, with the calcination conditions being able to be employed either during startup of the epoxidation or before startup.

The present invention therefore also provides, quite generally, for the use of this supported silver catalyst or the precursor thereof for preparing ethylene oxide by direct oxidation of ethene by means of oxygen and also provides a process for preparing ethylene oxide by direct oxidation of ethene by means of oxygen, wherein this supported silver catalyst or the precursor is used as oxidation catalyst.

Process for Preparing Ethylene Oxide

According to the invention, the oxidation of ethene to ethylene oxide can be carried out by all methods known to those skilled in the art. It is possible to use all reactors which can be used in the ethylene oxide production processes of the prior art, for example externally cooled shell-and-tube reactors or reactors having a loose catalyst bed and cooling tubes. The oxidation is preferably carried out in a tube reactor, preferably a shell-and-tube reactor.

As regards the reaction conditions, reference may be made, for example, to the disclosure on the subject in DE 25 21 906 A1, EP 0 014 457 A2, DE 2 300 512 A1, EP 0 172 565 A2, DE 24 54 972 A1, EP 0 357 293 A1, EP 0 266 015 A1, EP 0 085 237 A1, EP 0 082 609 A1, and EP 0 339 748 A2. Inert gases such as nitrogen and/or gases which are inert under the reaction conditions, e.g. steam, methane, and optionally reaction moderators such as halides, hydrocarbons such as ethyl chloride, vinyl chloride or 1,2-dichloroethane can in principle additionally be mixed into the reaction gas comprising ethane and oxygen. The oxygen content in the reactor is advantageously in such a range that no explosive gas mixture is present.

The above-described constituents of the reaction mixture can in each case optionally comprise small amounts of impurities. Ethene can, for example, be used in any purity grade which is suitable for the gas-phase oxidation according to the invention. Suitable purity grades of ethene are, for example, "polymer-grade" ethene which typically has a purity of at least 99%, or "chemical-grade" ethene which typically has a purity of 95% or less. The impurities typically comprise mainly ethane, propane and/or propene.

The oxidation of ethene to ethylene oxide is usually carried out at elevated temperature. Preference is given to temperatures in the range from 150 to 350° C., more preferably in the range from 180 to 300° C., more preferably temperatures in the range from 190° C. to 280° C. and particularly preferably temperatures in the range from 200° C. to 280° C.

The oxidation of ethene to ethylene oxide is preferably carried out at pressures in the range from 5 to 30 bar. The oxidation is more preferably carried out at a pressure in the range from 5 bar to 25 bar, more preferably at a pressure in the range from 10 bar to 20 bar and in particular in the range from 14 bar to 20 bar.

The oxidation is preferably carried out in a continuous process. If the reaction is carried out continuously, the GHSV (gas hourly space velocity) is, depending on the size of the reactor selected, for example on the size/cross-sectional area of the reactor, the shape and size of the catalyst, preferably in the range from 800/h to 10 000/h, preferably in the range from 2000/h to 6000/h, more preferably in the range from 2500/h to 5000/h, in each case based on the volume of the catalyst bed in the reactor.

The preparation of ethylene oxide from ethene and oxygen can be carried out in a circulation process. Here, the reaction mixture is circulated through the reactor and the newly formed ethylene oxide and the by-products formed in the reaction are removed from the product stream after each pass and the remaining product stream is supplemented with the required amounts of, for example, ethene, oxygen and/or reaction moderators and fed back into the reactor.

The separation of the ethylene oxide from the product stream and the optional subsequent work-up can be carried out by conventional methods of the prior art (cf. Ullmann's Encyclopedia of Industrial Chemistry, 5th edition, Vol. A-10, pp. 117-135, in particular pp. 123-125, VCH-Verlagsgesellschaft, Weinheim 1987).

Therefore, the present invention also relates to a process for preparing ethylene oxide by direct oxidation of ethene by means of oxygen wherein a supported silver catalyst as described above or a precursor of a supported silver catalyst as described above is used as catalyst.

The present invention includes the following embodiments, wherein these include the specific combinations of embodiments as indicated by the respective interdependencies defined therein:

1. A process for producing a supported silver catalyst, which comprises
    (a) reacting oxalic acid with an alkali metal base in a solvent, preferably water, to the second equivalence point of oxalic acid to give alkali metal oxalate;
    (b) reacting the alkali metal oxalate obtained according to (a) with a silver salt in a solvent, preferably water, to give silver oxalate;
    (c) forming a complex of the silver oxalate obtained according to (b) with a diamine compound in a solvent, preferably water, to give a diamine-silver oxalate complex.
2. The process according to embodiment 1, wherein the alkali metal base used in (a) is an alkali metal hydroxide, preferably potassium hydroxide, and wherein the silver salt used in (b) is silver nitrate.
3. The process according to embodiment 1 or 2, wherein (a) comprises:
    (a1) reacting oxalic acid with up to 98.5%, preferably from 90 to 98.5%, of the equimolar amount based on oxalic acid of alkali metal base in aqueous solution;
    (a2) bringing the aqueous solution obtained according to (a1) to a temperature in the range from 40 to 50° C., preferably from 40 to 45° C.;
    (a3) adding alkali metal base to the heated aqueous solution according to (a2) to the second equivalence point of oxalic acid, with the aqueous solution being maintained at a temperature in the range from 40 to 50° C., preferably from 40 to 45° C., during the addition.
4. The process according to embodiment 3, wherein (b) comprises;
    (b1) adding the aqueous solution obtained according to (a3) to an aqueous solution of the silver salt having a temperature in the range from 40 to 50° C., preferably from 40 to 45° C., to give a suspension comprising the silver oxalate;
    (b2) separating the silver oxalate from the suspension and washing of the silver oxalate which has been separated off with deionized water as washing water until the washings have an electrical conductivity of not more than 60 microsiemens/cm;
    (b3) concentrating the silver oxalate, preferably to a residual moisture content of the silver oxalate in the range from 10 to 25% by weight, based on silver oxalate.
5. The process according to any of embodiments 1 to 4, wherein the diamine compound used in (c) is an alkylene diamine having from 2 to 5 carbon atoms, preferably ethylene diamine.
6. The process according to any of embodiments 1 to 5, wherein the temperature in the reaction mixture present in the reaction according to (c) is set to values in the range from 10 to 30° C., preferably from 15 to 30° C.
7. The process according to any of embodiments 1 to 6, wherein the solution obtained according to (c) has a silver content, calculated as elemental silver, in the range from 25 to 32% by weight, based on the total weight of the solution.
8. The process according to any of embodiments 1 to 7 which additionally comprises
    (d) adding at least one promoter to the solution obtained according to (c).
9. The process according to embodiment 8, wherein lithium, cesium, tungsten, rhenium and sulfur are added as promoters and the solution obtained according to (d) has a lithium content in the range from 50 to 700 ppm by weight, a cesium content in the range from 50 to 1500 ppm by weight, a tungsten content in the range from 10 to 800 ppm by weight, a rhenium content in the range from 50 to 1200 ppm by weight and a sulfur content in the range from 2 to 100 ppm by weight.
10. The process according to any of embodiments 1 to 9 which additionally comprises
    (e) providing a porous support material which preferably comprises alpha-aluminum oxide, more preferably at least 98% by weight of alpha-aluminum oxide;
    (f) impregnating the porous support material with the solution obtained according to (c) or (d).
11. The process according to embodiment 10, wherein the porous support material has a cylindrical geometry, wherein a cylinder preferably has a length in the range from 5 to 10 mm, an external diameter in the range from 5 to 10 mm and a ratio of external diameter/mm to wall thickness/mm in the range from 2.5 to 4.5.
12. The process according to embodiment 10 or 11 which additionally comprises
    (g) calcining the impregnated support material obtained according to (f), preferably at a temperature in the range from 270 to 295° C.
13. A supported silver catalyst obtained or obtainable by a process according to embodiment 12 or a precursor of the supported silver catalyst obtained or obtainable by a process according to embodiment 10 or 11.
14. A supported silver catalyst according to embodiment 13 having a silver content in the range from 5 to 30% by weight, a lithium content in the range from 25 to 400 ppm by weight, a cesium content in the range from 25 to 750 ppm by weight, a tungsten content in the range from 5 to 500 ppm by weight, a rhenium content in the range from 25 to 600 ppm by weight and a sulfur content in the range from 0 to 50 ppm by weight applied to the porous support material by impregnation, in each case calculated as element and based on the total weight of the catalyst, wherein the porous support material has a cylindrical geometry, wherein a cylinder preferably has a length in the range from 5 to 10 mm, an external diameter in the range from 5 to 10 mm and a ratio of external diameter/mm to wall thickness/mm in the range from 2.5 to 4.5.
15. The use of a supported silver catalyst or a precursor thereof according to embodiment 13 or 14 for preparing ethylene oxide by direct oxidation of ethene by means of oxygen.

The present invention is illustrated by the following examples.

EXAMPLES

Example 1

Production of a Supported Silver Catalyst 1.1 Production of a Potassium Oxalate Solution 86.1 kg of oxalic acid dihydrate (Clariant, 99.9%) were dissolved in 517 kg of deionized water in a heatable stirred vessel. During the dissolution operation, 145.2 kg of a 47.5% strength by weight aqueous potassium hydroxide solution (deionized water) were quickly added by means of a weighed rough metering device. This amount corresponds to 90% of the amount of base required on an equimolar basis (ratio of oxalic acid dihydrate to KOH=1:2). The resulting solution was heated to 40° C. in the heatable stirred vessel by means of a hot water circuit which was in turn heated by means of steam. The temperature was measured by means of an internal temperature measurement, i.e. by direct measurement of the temperature of the solution.

Further 47.5% strength by weight aqueous potassium hydroxide solution was subsequently added slowly by means of a weighed fine metering device. When the second equivalence point of the deprotonation of oxalic acid was reached, the addition of the potassium hydroxide solution was stopped. The end point determination, i.e. the determination of the second equivalence point, was carried out by measurement of the pH in the stirred vessel by means of a glass electrode (Mettler-Toledo, InPro® 3250/225 Pt 1000). Here, the pH was monitored on-line from the commencement of addition of the potassium hydroxide solution. According to the invention, the addition of the potassium hydroxide solution was stopped when a pH of 8.52 was reached.

1.2 Providing a Silver Nitrate Solution

An aqueous silver nitrate solution having a temperature in the region of 44° C. was placed in a stirred precipitation vessel which had a volume of 1800 l and was maintained at a temperature in the region of 44° C. The silver nitrate solution was produced by dissolving 219 kg of $AgNO_3$ in 597 kg of $H_2O$ (deionized water).

1.3 Precipitation

The potassium oxalate solution produced as described in 1.2 was transferred via a downward-slanting conduit into the stirred precipitation vessel which comprised the above-described silver nitrate solution and was maintained at a temperature in the region of 44° C. over a period of 4 hours. The precipitation of silver oxalate was induced by the addition of the potassium oxalate solution. After a precipitation time of 4 hours and a further stirring time of 1 hour, the reaction was complete.

1.4 Filtration

The precipitated solid obtained as described in 1.3 was filtered off on a membrane filter press and washed with deionized water until the conductivity of the washings had reached a value of (not more than) 40 microsiemens/cm (conductivity measuring instrument from WTW, model LF 323, Elektrode Tetra Con 325). The filter cake was then pressed further under a water pressure of 4 bar until no more water flowed from the washing water lines of the filter press. The filter cake obtained in this way was taken out and weighed. The residual moisture content of the filter cake was determined by means of a moisture determination instrument (IR dryer: Mettler Toledo HB43). About 220 kg of moist silver oxalate having a residual moisture content of about 15% by weight were obtained in this way (for precise amounts and moisture contents: see item 1.5 below).

This sequence described in items 1.1 to 1.3 was carried out a total of four times. In this way, about 840 kg of silver oxalate were provided for the subsequent complexation described below.

1.5 Complexation

The starting materials for the complexation of four filter cakes were calculated on the basis of the mass and the residual moisture content of the first filter cake obtained. Ethylenediamine was used as complexing agent. The ethylenediamine was used as an aqueous solution in deionized water having a concentration of 60% by weight.

Complexation will be described below for the example of the first filter cake having a mass of 215.2 kg and a residual moisture content of 13.6% by weight determined as described above:

i) 759.4 kg of ethylenediamine (EDA), 60% strength by weight in deionized water, and 136 kg of deionized water were placed in a coolable stirred vessel.

ii) the first filter cake (215.2 kg, residual moisture content 13.6% by weight) was added to the EDA solution in such a way that the temperature in the stirred vessel which had been cooled to 15° C. did not exceed 30° C.

iii) the three further filter cakes (see 1.4 above: carrying out of the sequence four times) were subsequently added in succession. These three filter cakes had a weight of 219.4 kg at a residual moisture content of 14.7% by weight, a weight of 220.8 kg at a residual moisture content of 14.5% by weight and a weight of 187 kg at a residual moisture content of 14.9% by weight.

iv) 1738 kg of complex solution having a density of 1.504 g/ml and a silver content, calculated as elemental silver, of 28.47% by weight were obtained.

1.6 Addition of Promoters

The weights of the promoters to be added were calculated from the density and concentration of the silver solution and the water uptake of the support (see below, item 1.7). The promoters lithium and sulfur, and separately therefrom, tungsten and cesium were in each case present in an aqueous solution, while rhenium was present as another separate aqueous solution. Salts used were: $LiNO_3$ (Merck, 99.50% pure) and $(NH_4)_2SO_4$ (Aldrich, 99.99% pure) for the first aqueous solution, $H_2WO_4$ (Aldrich, 99.999% pure) and CsOH (Aldrich, 99% pure; solution in 50% of water) for the second aqueous solution and $NH_4ReO_4$ (Alfa Aesar, 99.999% pure) for the third aqueous solution.

Li (as $LiNO_3$ solution, 2.85%)+S (as $(NH_4)_2SO_4$ solution 0.21%): 21.95 kg

W (as $H_2WO_4$ solution, 2.00%)+Cs (as CsOH solution, 4.00%): 32.94 kg

Re (as $NH_4ReO_4$ solution, 4.10%): 30.53 kg

The amounts of promoters weighed in were added while stirring to the stirred vessel comprising the complex solution obtained as described in 1.5 (order: Li/S, then W/Cs, then Re). The mixture was stirred for 1 hour in order to make homogeneous mixing possible.

1.7 Impregnation of a Support

An alpha-aluminum oxide support having a bimodal pore size distribution was used as support; the two corresponding peak maxima, determined by mercury porosimetry, were at 0.95 and 53.2 microns. The support had the following contents, in each case in ppm by weight: Ca (300), K (300), Mg (100), Na (400), Si (600), Zr (<100), Ti (<100), Zn (<100), Fe (200). The water uptake of the support was 0.444 ml/g, the BET surface area was 0.82 $m^2/g$, and the C value was 132, determined in accordance with DIN ISO 9277. The support had a cylindrical geometry, with the cylinders having an external diameter of 7.97 mm, a length of 8.38 mm and a ratio of external diameter/mm to wall thickness/mm of 2.91.

Impregnation of the support was carried out in a vacuum tumble mixer having a volume of 1.8 $m^3$. 695 kg of dry support were impregnated four times under a reduced pressure of 50 mbar and at a rate of rotation of 0.5 revolutions/min. Impregnation was carried out at room temperature over a period of 4 hours. The vacuum was then broken and the impregnated catalyst was introduced into 200 l drums having a PE polymer in-liner.

1.8 Calcination

A total of 15 kg of the impregnated support were treated in 500 g batches at 283° C. under 8.3 m³ of air per hour in a convection furnace (from HORO, model 129 ALV-SP, catalog No.: 53270) for 12 minutes. The calcined catalyst comprised 15.5% of Ag, 190 ppm of Li, 14 ppm of S, 200 ppm of W, 400 ppm of Cs, 380 ppm of Re, in each case calculated as element.

Example 2

Production of a Supported Silver Catalyst

2.1 Production of a Potassium Oxalate Solution 216.33 g of oxalic acid dihydrate (Clariant 99.9%) were dissolved in 1.29 l of deionized water in a 3 l glass beaker. During the dissolution operation, 395.1 g of a 47.8% strength by weight aqueous potassium hydroxide solution (deionized water) were added, corresponding to 98.1% of the amount of base required on an equimolar basis (ratio of oxalic acid dihydrate to KOH=1:2). This solution was heated to 40° C. by means of an electric hotplate (magnetic stirrer). The temperature was measured by means of an internal temperature measurement, i.e. by direct measurement of the temperature of the solution.

To prepare for the subsequent titration, 5 drops of a 0.2% strength ethanolic phenolphthalein solution were added as indicator. The titration was carried out by slow addition of further aqueous potassium hydroxide solution. To ensure finer metering during the titration, the 47.8% strength by weight KOH solution as used above was diluted by means of deionized water to a KOH concentration of 20% by weight and this diluted KOH solution was added. The end point of the titration is indicated by the second equivalence point of the deprotonation of oxalic acid. This point could readily be detected by the change in color of the color indicator from colorless to pink for the purposes of rough monitoring. As a further determination of the second equivalence point, the pH was monitored. A Portamess® pH meter from Knick was used for this purpose. The addition of the KOH solution was stopped at a pH of 8.59 as determined by this pH meter.

2.2 Production of a Silver Nitrate Solution 1.5 l of deionized water were placed in a 5 l brown glass beaker. While stirring (two-stage blade stirrer, 300 revolutions/min), 550.03 g of AgNO₃ (purity: 99.9%; Johnson-Matthey) were added and dissolved completely. During this procedure, the solution was heated to 40° C.

2.3 Precipitation

The aqueous potassium oxalate solution obtained as described in 2.1 and having a temperature of 40° C. was added by means of a metering pump to the AgNO₃ solution (40° C.) obtained as described in 2.2 over a period of about 45 minutes (volume flow=about 33 ml/min). The suspension (light-grey/brown) became viscous after about 20 minutes, unstirrable after about 30 minutes and fluid again toward the end of the addition. After addition of all the potassium oxalate solution, the mixture was stirred at 40° C. for another 1 hour.

2.4 Filtration

In a suction apparatus (5 l filter flask), reduced pressure was applied to a 1 l suction filter and all of the silver oxalate suspension obtained as described in 2.3 was transferred a little at a time into the suction filter. When there was no longer any liquid above the filter cake, air was admitted into the filter flask. 1 l of deionized water was in each case carefully introduced into the suction filter and reduced pressure was again applied. The filter cake was washed with these 1 l portions of water until the conductivity of the washings had reached a value of (not more than) 40 microsiemens/cm (conductivity measuring instrument from WTW, model LF 323, Electrode Tetra Con 325). During the last washing operation, suction was applied until no more water dripped from the suction filter. The filter cake was transferred into a porcelain dish, the residual moisture content of the filter cake was determined and the filter cake was weighed. The residual moisture content of the filter cake was determined by means of a moisture determination instrument (IR dryer: Mettler Toledo HB43). 614.43 g of moist silver oxalate having a residual moisture content of 21.20% by weight were obtained in this way.

2.5 Complexation 305.4 g of ethylenediamine (EDA) were placed in a 2 l glass beaker and cooled to 10° C. in an ice bath. 241.3 g of deionized water were then added in small portions. The addition was carried out in such a way that the temperature of the solution was not more than 35° C. After the addition of water was complete, 484.2 g of the filter cake obtained as described in 2.4 and having a residual moisture content of 21.20% by weight were added in small portions over a period of about 75 minutes. The temperature was basically in the range from 20 to 30° C. and never exceeded 30° C. After the addition was complete, the glass beaker was covered with Parafilm, protected from light and stirred overnight at room temperature. The dark grey solution obtained was subsequently centrifuged.

The clear solution had an Ag content determined by refractometry of 29.66% by weight, calculated as elemental silver, and a density of 1.533 g/ml.

2.6 Promoters

The weights of the promoters to be added were calculated from the density and concentration of the silver solution and the water uptake of the support (see below, item 2.7). The promoters lithium and sulfur, and separately therefrom, tungsten and cesium were in each case present in an aqueous solution, while rhenium was present as another separate aqueous solution. Salts used were: LiNO₃ (Merck, 99.50% pure) and (NH₄)₂SO₄ (Aldrich, 99.99% pure) for the first aqueous solution, H₂WO₄ (Aldrich, 99.999% pure) and CsOH (Aldrich, 99% pure; solution in 50% of water) for the second aqueous solution and NH₄ReO₄ (Alfa Aesar, 99.999% pure) for the third aqueous solution.

2.7 Impregnation

An alpha-aluminum oxide support having a bimodal pore size distribution was used as support; the two corresponding peak maxima, determined by mercury porosimetry, were at 1.26 and 60.9 microns. The support had the following contents, in each case in ppm by weight: Ca (600), K (200), Mg (100), Na (200), Si (500), Zr (<100), Ti (<100), Zn (<100), Fe (100). The water uptake of the support was 0.441 ml/g, the BET surface area was 0.65 m²/g, and the C value was 114, determined in accordance with DIN ISO 9277. The support had a cylindrical geometry, with the cylinders having an external diameter of 6.04 mm, a length of 5.55 mm and a ratio of external diameter/mm to wall thickness/mm of 3.3. 100.02 g of this support were weighed into a flask (1 l pear-shaped flask having 4 integrated baffles). The flask which had been filled in this way was clamped onto a rotary evaporator. After evacuation, the flask was rotated at 30 revolutions min at a pressure of less than 20 mbar. The complex solution obtained as in 2.5 was weighed into a glass beaker, the promoters and the water were weighed in and the solution obtained was stirred for 5 minutes. The solution was dripped onto the support over a period of 15 minutes. The following amounts were used:

Complex solution according to 2.5: 61,9274 g

Li (as LiNO₃ solution, 2.85%)+S (as (NH₄)₂SO₄ solution, 0.21%): 0.7929 g

W (as $H_2WO_4$ solution, 1.00%)+Cs (as CsOH solution, 3.50%): 1.1890 g

Re (as $NH_4ReO_4$ solution, 3.10%): 1.1877 g $H_2O$: 0.5551 g

Support: 100.02 g

The impregnated supports were subsequently rotated under reduced pressure for a further 15 minutes. Air was then admitted to the apparatus, the flask was taken off, closed by means of a stopper and stored for 1 hour before calcination (see 2.8 below). During this time, the contents of the flask were mixed gently every 15 minutes.

2.8 Calcination

The impregnated support was treated at 283° C. under 8.3 $m^3$ of air per hour in a convection furnace (from HORO, model 129 ALV-SP, catalog No.: 53270) for 12 minutes.

Example 3

Production of a Supported Silver Catalyst
(Comparative Example)

3.1 Production of a Potassium Oxalate Solution 402.67 g of potassium hydroxide were mixed with 1290 ml of deionized water with stirring in a 3 l glass beaker. 216.33 g of oxalic acid dihydrate were added thereto (Clariant, 99.9%) and dissolved completely. The weight ratio of potassium hydroxide to oxalic acid dihydrate corresponded to the theoretical, calculated value necessary for complete conversion of the oxalic acid used into potassium oxalate. The solution was maintained at a temperature of 40° C. during mixing.

3.2 to 3.8

All further steps 3.2 to 3.8 were carried out in a manner identical to the steps 2.2 to 2.8. The following amounts were used:

Complex solution (Ag content: 28.93% by weight, density: 1.530 g/ml): 63.1000 g

Li (as $LiNO_3$ solution, 2.85%)+S (as $(NH_4)_2SO_4$ solution, 0.21%): 0.7919 g W (as $H_2WO_4$ solution, 1.00%)+Cs (as CsOH solution, 3.50%): 1.1857 g Re (as $NH_4ReO_4$ solution, 4.10%): 0.8989 g Support: 100.09 g

Example 4

Catalyst Test 4.1 General Production of Crushed Catalyst Material

The catalyst cylinders obtained were roughly crushed in a porcelain dish by means of a mortar. The comminuted material was subsequently brought to the desired particle size fraction (0.5-0.9 mm) by means of a sieving machine, round sieve and balls.

4.2 General Method of Testing the Catalysts (Epoxidation of Ethylene)

The epoxidation was carried out in an experimental reactor comprising a vertical reaction tube made of stainless steel and having an internal diameter of 6 mm and a length of 2200 mm. The reaction tube provided with a jacket was heated by means of hot oil having the temperature T(oil) which flowed through the jacket. To a very good approximation, the temperature of the oil corresponded to the temperature in the reaction tube and thus the reaction temperature. The reaction tube was filled from the bottom upward to a height of 212 mm with inert steatite balls (diameter 1.0-1.6 mm), above that to a height of 1100 mm with 38.2 g of crushed catalyst material, particle size 0.5-0.9 mm, and above that to a height of 707 mm with inert steatite balls (1.0-1.6 mm). The feed gas entered the reactor from above and left the reactor again at the lower end after passing through the catalyst bed. The feed gas comprised 35% by volume of ethylene, 7% by volume of oxygen, 1% by volume of $CO_2$. At the beginning, 2.5 ppm of EC (ethylene chloride) were used for start-up. Depending on the catalyst and performance, the EC concentration was increased every 24 hours to a maximum of 8 ppm. The remainder of the feed gas was methane.

The experiments were carried out at a pressure of 15 bar and a gas hourly space velocity (GHSV) of 4750 l/h and an ethylene oxide (EO) space-time yield of 250 kg of EO/(($m^3$ of cat)×h). The reaction temperature was regulated so as to give the prescribed ethylene oxide concentration in the offgas of 2.7%. To optimize the catalyst in respect of selectivity and conversion, from 2.2 to 8.0 ppm of ethylene chloride were added as moderator to the feed gas. The gas leaving the reactor was analyzed by means of on-line MS. The selectivity of the catalyst was determined from the results of the analysis.

4.3 Results

Composition of the catalysts according to Examples 2 and 3: the calcined catalysts comprised 15.5% of Ag, 190 ppm of Li, 14 ppm of S, 200 ppm of W, 350 ppm of Cs, 310 ppm of Re and were, as indicated in Examples 2 and 3, prepared in different ways.

TABLE 1

Performance results for the catalysts examined

| | Method of preparation | Selectivity [%, 332 h] | Temperature [° C. 332 h] |
|---|---|---|---|
| Example 1 | Titration (large batch) | 90.6 | 245.0 |
| Example 2 | Titration (laboratory batch) | 90.6 | 244.5 |
| Example 3 (comparison) | Without titration | 89.9 | 243.0 |

It could be shown that the use of an acid-base titration in the production of the potassium oxalate solution has a positive effect on the selectivity of the silver catalyst. Compared to the catalyst produced using an equimolar potassium oxalate solution without acid-base titration, a selectivity improved by up to 0.7% at a comparable activity could be detected.

Example 5

Preparation of Sliver Oxalate (Comparative Example)

To show the advantages of the process of the invention in which oxalic acid is reacted with an alkali metal base in a solvent, preferably water, to the second equivalence point of oxalic acid to give alkali metal oxalate, 4 different aqueous potassium oxalate solutions were produced according to the prior art.

Here, the theoretically required amounts of starting materials on a laboratory scale were calculated in each case from the same batches of starting materials (cf. also Example 3, item 3.1) and weighed out. In each case, 315.74 g of aqueous potassium hydroxide solution having a potassium hydroxide concentration of 47.5% by weight and 168.9 g of oxalic acid dihydrate were used, and the amount of water was 1015 g.

The potassium oxalate solutions resulting in each case (each about 1.5 kg) having a temperature of 40° C. were then added over a period of 45 minutes to a silver nitrate solution which had been provided in a reactor and brought to a temperature of 40° C.

The following experimental parameters according to Table 2 were followed:

TABLE 2

Comparative examples for the precipitation of silver oxalate

| Experiment No. | Amount weighed into reactor/g | | Composition of the potassium oxalate solution/g | | | Addition time/min | Further stirring time/min |
|---|---|---|---|---|---|---|---|
| | AgNO$_3$ | H$_2$O | KOH*$^)$ | ODH**$^)$ | H$_2$O | | |
| 090721 | 429.56 | 1171.52 | 315.74 | 168.9 | 1015 | 45 | 1.0 |
| 090827 | 429.62 | 1171.52 | 315.74 | 168.9 | 1015 | 45 | 1.0 |
| 091001 | 429.56 | 1171.52 | 315.74 | 168.9 | 1015 | 45 | 1.0 |
| 091027 | 429.56 | 1171.52 | 315.74 | 168.9 | 1015 | 45 | 1.0 |

*$^)$aqueous potassium hydroxide solution, potassium hydroxide concentration of 47.5% by weight
**$^)$oxalic acid dihydrate The course of the pH over time was determined by means of a pH meter from the commencement of the addition of the potassium oxalate solutions. At the same weights of starting materials and with calculation of the desired equimolar composition, extremely different final pH values after precipitation after 45 minutes resulted in the various precipitation suspensions (silver oxalate suspensions), as can clearly be seen from FIG. 1. It may be remarked that monitoring the pH of the precipitant solution (potassium oxalate solution) according to the invention resulted in final pH values which were all within a very narrow window of pH 5.5+/−0.4 pH units.

In addition, it has been found that time periods and local zones with high pH values of greater than 9-10 frequently occur during the precipitation because of the addition of an alkaline potassium oxalate solution without setting of the pH according to the invention, and also because of the precipitation suspension becoming viscous. This too can clearly be seen in FIG. 1. In addition the pH electrode becomes contaminated very quickly and indicates unreliable values.

In experiment 091001, the amount of silver oxide/hydroxide formed in the precipitation of the silver oxalate was also determined. The concentration of silver oxide/hydroxide found was 0.2% by weight, based on the mass of the suspension. This corresponded to a loss of 2% of silver oxalate, which can ultimately be attributed to the excessively high pH of the potassium hydroxide solution used. This problem can successfully be countered by means of the titration according to the invention since this avoids an excess or deficiency of hydroxide and thus a pH of the potassium oxalate precipitation solution which is too high or too low, which would lead to increased silver oxide/hydroxide formation or to the situation where not all the silver precipitates as silver oxalate but partly remains in solution as silver nitrate, by the targeted reaction to the second equivalence point of oxalic acid. For this reason, both a pH which is too high and a pH which is too low lead to an undesirable loss of valuable silver.

Figure 1:
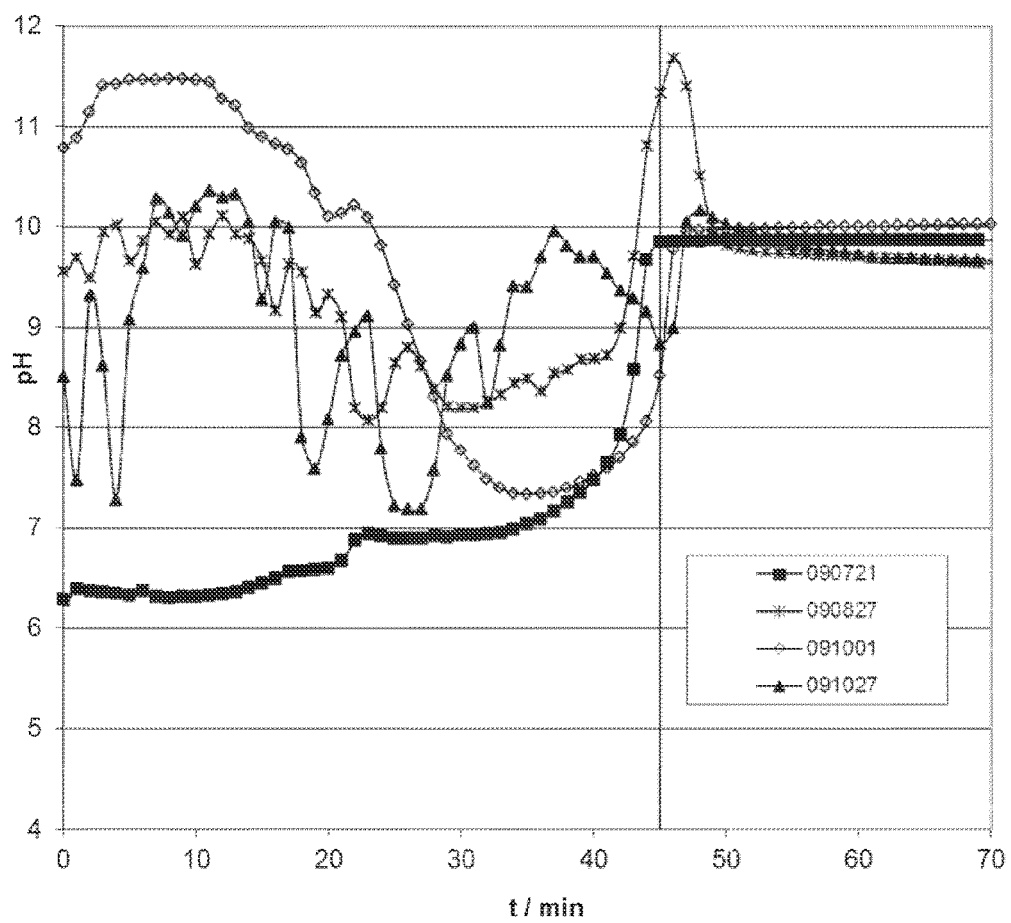
FIG. 1 shows the course of the in the reaction mixture during the introduction of potassium oxalate solutions for the 4 individual experiments in Example 5. The addition time in minutes is shown on the x axis and the corresponding measured pH is shown on the y axis. The addition is complete after 45 minutes; this point in time is indicated by the vertical line at 45 minutes. It can clearly be seen that the pH values of potassium oxalate solutions which have been produced by weighing out of the substances potassium hydroxide and oxalic acid and not by means of the titration according to the invention differ considerably from one another.
Figure 2:
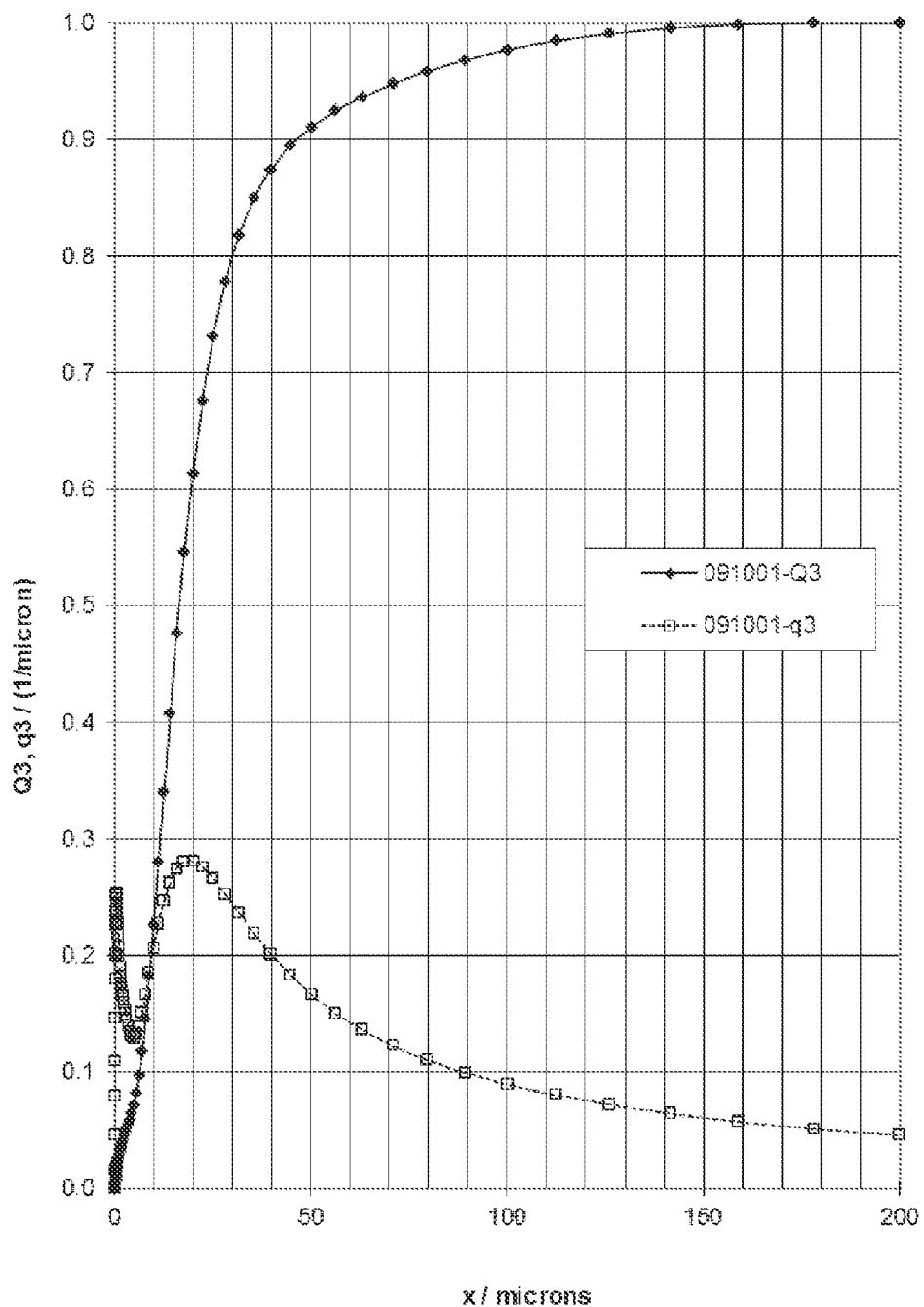
FIG. 2 shows the resulting particle sizes of the silver oxalate determined for an individual experiment (091001) of Example 5. The resulting particle size is characterized by an $x_{50.3}$ of <20 microns (50% of the total mass of the particles of the sample have a diameter of less than 20 microns). The particle size in microns is shown on the x axis and the cumulative distribution $Q_3$ of the particle mass (symbol: black diamond) and the corresponding density distribution $q_3$ (first derivative of $Q_3$; symbol: open square) are shown on the y axis.

The invention claimed is:

1. A process for producing a supported silver catalyst, which comprises
   (a) reacting oxalic acid with an alkali metal base in a solvent to the second equivalence point of oxalic acid to give alkali metal oxalate;
   (b) reacting the alkali metal oxalate obtained according to (a) with a silver salt in a solvent to give silver oxalate;
   (c) forming a complex of the silver oxalate obtained according to (b) with a diamine compound in a solvent to give a diamine-silver oxalate complex.

2. The process according to claim 1, wherein the alkali metal base used in (a) is an alkali metal hydroxide, and wherein the silver salt used in (b) is silver nitrate.

3. The process according to claim 1, wherein (a) comprises:
   (a1) reacting oxalic acid with up to 98.5% of the equimolar amount based on oxalic acid of alkali metal base in aqueous solution;
   (a2) bringing the aqueous solution obtained according to (a1) to a temperature in the range from 40 to 50° C.;
   (a3) adding alkali metal base to the heated aqueous solution according to (a2) to the second equivalence point of oxalic acid, with the aqueous solution being maintained at a temperature in the range from 40 to 50° C. during the addition.

4. The process according to claim 3, wherein (b) comprises:
   (b1) adding the aqueous solution obtained according to (a3) to an aqueous solution of the silver salt having a temperature in the range from 40 to 50° C. to give a suspension comprising the silver oxalate;
   (b2) separating the silver oxalate from the suspension and washing of the silver oxalate which has been separated off with deionized water as washing water until the washings have an electrical conductivity of not more than 60 microsiemens/cm;
   (b3) concentrating the silver oxalate.

5. The process according to claim 1, wherein the diamine compound used in (c) is an alkylene diamine having from 2 to 5 carbon atoms.

6. The process according to claim 1, wherein the temperature in the reaction mixture present in the reaction according to (c) is set to values in the range from 10 to 30° C.

7. The process according to claim 1, wherein the solution obtained according to (c) has a silver content, calculated as elemental silver, in the range from 25 to 32% by weight, based on the total weight of the solution.

8. The process according to claim 1, which additionally comprises
(d) adding at least one promoter to the solution obtained according to (c).

9. The process according to claim 8, wherein lithium, cesium, tungsten, rhenium and sulfur are added as promoters and the solution obtained according to (d) has a lithium content in the range from 50 to 700 ppm by weight, a cesium content in the range from 50 to 1500 ppm by weight, a tungsten content in the range from 10 to 800 ppm by weight, a rhenium content in the range from 50 to 1200 ppm by weight and a sulfur content in the range from 2 to 100 ppm by weight.

10. The process according to claim 1, which additionally comprises
(e) providing a porous support material which preferably comprises alpha-aluminum oxide;
impregnating the porous support material with the solution obtained according to (c) or (d).

11. The process according to claim 10, wherein the porous support material has a cylindrical geometry.

12. The process according to claim 10, which additionally comprises
(g) calcining the impregnated support material obtained according to (f).

13. The process according to claim 1, which comprises
(a) reacting oxalic acid with an alkali metal base in a solvent to the second equivalence point of oxalic acid to give alkali metal oxalate;
(b) reacting the alkali metal oxalate obtained according to (a) with a silver salt in a solvent to give silver oxalate;
(c) forming a complex of the silver oxalate obtained according to (b) with a diamine compound in a solvent to give a diamine-silver oxalate complex;
and which additionally comprises
(d) adding at least one promoter to the solution obtained according to (c);
(e) providing a porous support material;
impregnating the porous support material with the solution obtained according to (c) or (d);
(g) calcining the impregnated support material obtained according to (f).

14. The process according to claim 1, which comprises
(a) reacting oxalic acid with an alkali metal base in a solvent to the second equivalence point of oxalic acid to give alkali metal oxalate;
(b) reacting the alkali metal oxalate obtained according to (a) with a silver salt in a solvent to give silver oxalate;
(c) forming a complex of the silver oxalate obtained according to (b) with a diamine compound in a solvent to give a diamine-silver oxalate complex;
and which additionally comprises
(d) adding at least one promoter to the solution obtained according to (c);
(e) providing a porous support material;
(f) impregnating the porous support material with the solution obtained according to (c) or (d);
(g) calcining the impregnated support material obtained according to (f);
wherein (a) comprises:
(a1) reacting oxalic acid with up to 98.5% of the equimolar amount based on oxalic acid of alkali metal base in aqueous solution;
(a2) bringing the aqueous solution obtained according to (a1) to a temperature in the range from 40 to 50° C.;
(a3) adding alkali metal base to the heated aqueous solution according to (a2) to the second equivalence point of oxalic acid, with the aqueous solution being maintained at a temperature in the range from 40 to 50° C. during the addition;
and wherein (b) comprises:
(b1) adding the aqueous solution obtained according to (a3) to an aqueous solution of the silver salt having a temperature in the range from 40 to 50° C. to give a suspension comprising the silver oxalate;
(b2) separating the silver oxalate from the suspension and washing of the silver oxalate which has been separated off with deionized water as washing water until the washings have an electrical conductivity of not more than 60 microsiemens/cm;
(b3) concentrating the silver oxalate, preferably to a residual moisture content of the silver oxalate in the range from 10 to 25% by weight, based on silver oxalate.

15. The process according to claim 1, which comprises
(a) reacting oxalic acid with an alkali metal base in water to the second equivalence point of oxalic acid to give alkali metal oxalate;
(b) reacting the alkali metal oxalate obtained according to (a) with a silver salt in water to give silver oxalate;
(c) forming a complex of the silver oxalate obtained according to (b) with a diamine compound in water to give a diamine-silver oxalate complex;
and which additionally comprises
(d) adding at least one promoter to the solution obtained according to (c);
(e) providing a porous support material which comprises at least 98% by weight of alpha-aluminum oxide;
(f) impregnating the porous support material with the solution obtained according to (c) or (d);
(g) calcining the impregnated support material obtained according to (f), at a temperature in the range from 270 to 295° C.;
wherein (a) comprises:
(a1) reacting oxalic acid with from 90 to 98.5%, of the equimolar amount based on oxalic acid of alkali metal base in aqueous solution;
(a2) bringing the aqueous solution obtained according to (a1) to a temperature in the range from 40 to 45° C.;
(a3) adding alkali metal base to the heated aqueous solution according to (a2) to the second equivalence point of oxalic acid, with the aqueous solution being maintained at a temperature in the range from 40 to 45° C., during the addition;
and wherein (b) comprises:
(b1) adding the aqueous solution obtained according to (a3) to an aqueous solution of the silver salt having a temperature in the range from 40 to 45° C., to give a suspension comprising the silver oxalate;
(b2) separating the silver oxalate from the suspension and washing of the silver oxalate which has been separated off with deionized water as washing water until the washings have an electrical conductivity of not more than 60 microsiemens/cm;

(b3) concentrating the silver oxalate to a residual moisture content of the silver oxalate in the range from 10 to 25% by weight, based on silver oxalate.

16. The process according to claim 1, wherein the diamine compound used in (c) is ethylene diamine.

* * * * *